US011946866B2

United States Patent
Yamada et al.

(10) Patent No.: US 11,946,866 B2
(45) Date of Patent: Apr. 2, 2024

(54) FLUORESCENCE IMAGE ANALYZING APPARATUS, METHOD OF ANALYZING FLUORESCENCE IMAGE, AND COMPUTER PROGRAM

(71) Applicant: SYSMEX CORPORATION, Kobe (JP)

(72) Inventors: Kazuhiro Yamada, Kobe (JP); Shohei Matsumoto, Kobe (JP); Yusuke Konishi, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 17/345,645

(22) Filed: Jun. 11, 2021

(65) Prior Publication Data

US 2021/0302315 A1 Sep. 30, 2021

Related U.S. Application Data

(63) Continuation of application No. 15/951,562, filed on Apr. 12, 2018, now Pat. No. 11,085,880.

(30) Foreign Application Priority Data

Apr. 14, 2017 (JP) ................. 2017-080855

(51) Int. Cl.
*G06K 9/00* (2022.01)
*C12Q 1/6841* (2018.01)
(Continued)

(52) U.S. Cl.
CPC ....... *G01N 21/6428* (2013.01); *C12Q 1/6841* (2013.01); *G01N 21/6456* (2013.01);
(Continued)

(58) Field of Classification Search
CPC .............. C12Q 1/6841; C12Q 2543/10; C12Q 2543/101; C12Q 2563/107; C12Q 1/6876;
(Continued)

(56) References Cited

U.S. PATENT DOCUMENTS

| 2014/0153811 A1* | 6/2014 | Seppo ................... G06T 7/0014 382/133 |
| 2014/0205173 A1* | 7/2014 | Padfield ................. G06V 20/69 382/133 |
| 2021/0285056 A1* | 9/2021 | Chukka .................. G16B 25/10 |

FOREIGN PATENT DOCUMENTS

| JP | 2016-164540 A | 9/2016 |
| WO | 02/093130 A2 | 11/2002 |

OTHER PUBLICATIONS

Qinghua Du et al., "Calibration of Interphase Fluorescence In Situ Hybridization Cutoff by Mathematical Models", Cytometry Part A, First published on Nov. 18, 2015, pp. 239-245, vol. 89, No. 3, International Society for Advancement of Cytometry.
(Continued)

*Primary Examiner* — Atiba O Fitzpatrick
(74) *Attorney, Agent, or Firm* — Crowell & Moring LLP

(57) ABSTRACT

Disclosed is a fluorescence image analyzing apparatus including a light source that emits light to a sample including a plurality of cells labeled with a fluorescent dye at a target site, an imaging unit that captures a fluorescence image of each of the cells that emit fluorescence by being irradiated with the light, a fluorescence image of the cell, and a processing unit that processes the fluorescence image captured by the imaging unit to acquire a bright spot pattern of fluorescence in the fluorescence image. The processing unit selects a reference pattern corresponding to a measurement item of the sample from a plurality of reference patterns corresponding to a plurality of measurement items and generates information used for determination of the sample (Continued)

based on the bright spot pattern of fluorescence in the fluorescence image and the selected reference pattern.

20 Claims, 15 Drawing Sheets

(51) Int. Cl.
   *G01N 21/64* (2006.01)
   *G06T 7/00* (2017.01)
   *G02B 21/16* (2006.01)
   *G02B 21/36* (2006.01)
   *G02B 27/10* (2006.01)
   *G02B 27/14* (2006.01)

(52) U.S. Cl.
   CPC ....... *G01N 21/6458* (2013.01); *G06T 7/0014* (2013.01); *G01N 2021/6439* (2013.01); *G01N 2021/6441* (2013.01); *G02B 21/16* (2013.01); *G02B 21/365* (2013.01); *G02B 27/1006* (2013.01); *G02B 27/141* (2013.01); *G06T 2207/10056* (2013.01); *G06T 2207/30024* (2013.01)

(58) Field of Classification Search
   CPC .. C12Q 1/6881; C12Q 1/6883; C12Q 1/6886; C12Q 1/6879; C12Q 2537/143; G01N 21/6428; G01N 2021/6439; G01N 2021/6441; G01N 21/6456; G01N 21/6458; G01N 2021/6421; G01N 27/44726; G01N 15/1468; G01N 15/147; G01N 2015/1472; G01N 15/1475; G02B 21/16; G02B 21/365; G02B 21/367; G06T 2207/10064; G06T 7/0014; G06T 7/0016; G06T 7/001; G06T 7/248; G06T 7/337; G06T 7/74; G06T 2207/10056; G06T 2207/10061; G06T 2207/30024; G06T 7/0012; G06T 2207/30242; G16B 25/10; G06V 20/69; G06V 20/698; G06V 20/693; G06V 20/695
   See application file for complete search history.

(56) References Cited

OTHER PUBLICATIONS

The Communication pursuant to Article 94(3) EPC dated Oct. 26, 2021 in a counterpart European patent application No. 18166771.8.
The Japanese Office Action dated Sep. 13, 2022, in a counterpart Japanese patent application No. 2021-152591.
Communication pursuant to Article 94(3) EPC, dated Mar. 29, 2023, pp. 1-8, issued in European patent application No. 18166771.8, European Patent Office, Munich Germany.

* cited by examiner

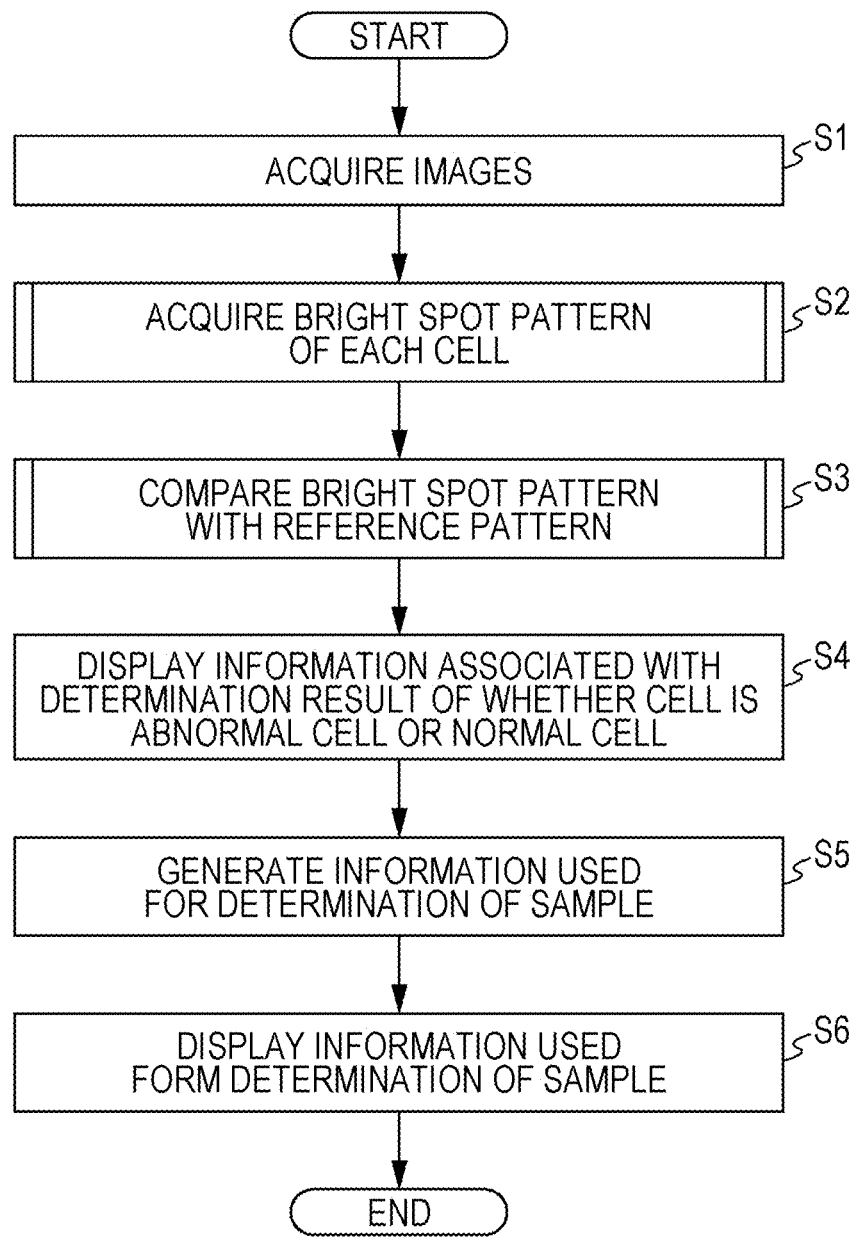

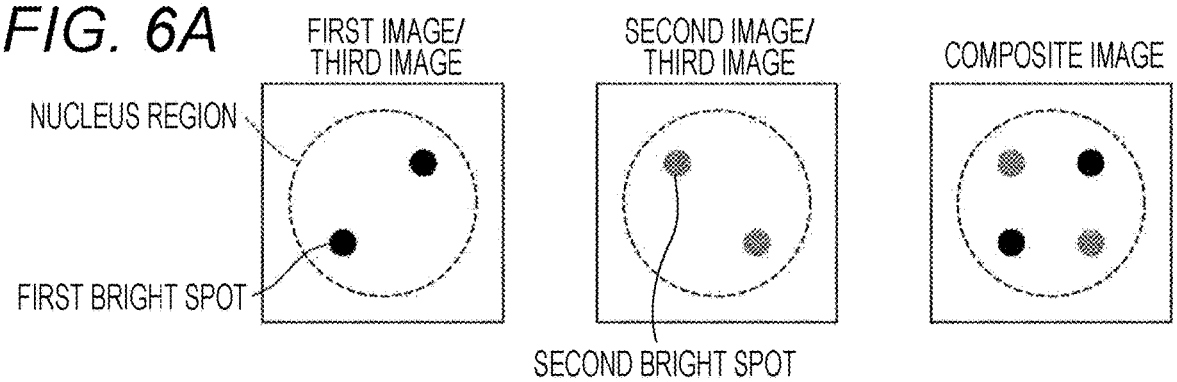
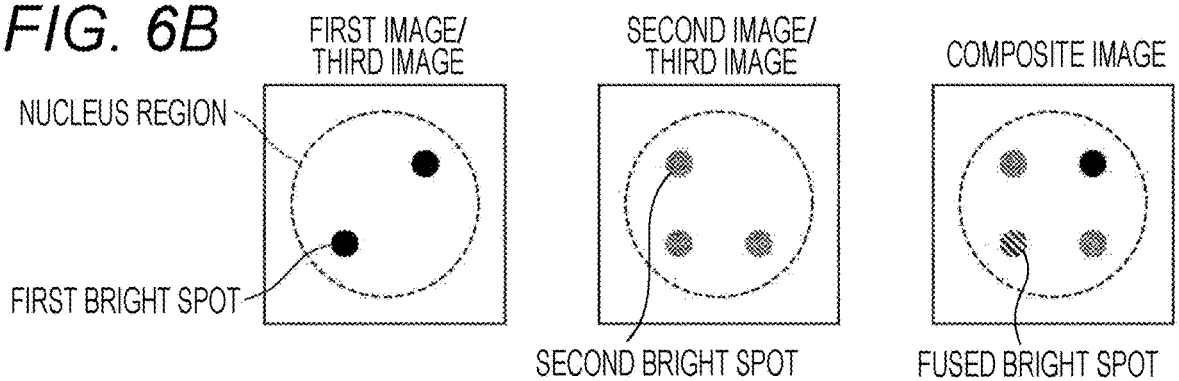
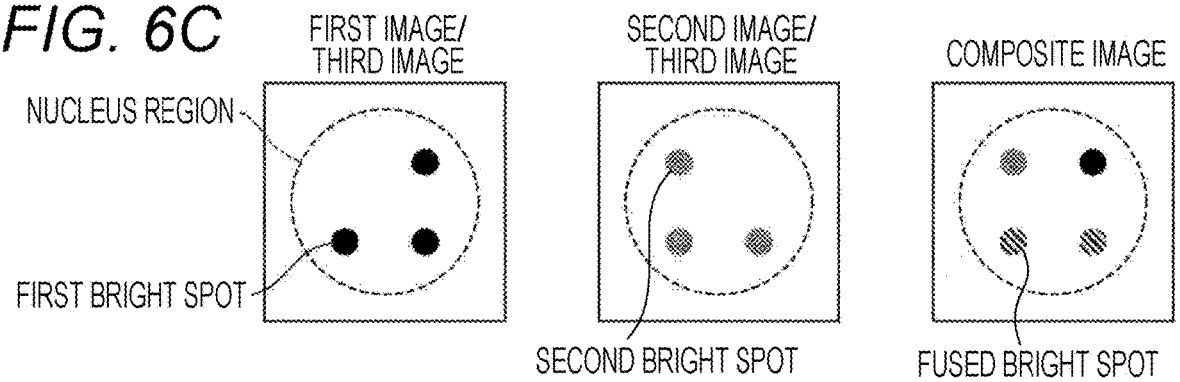
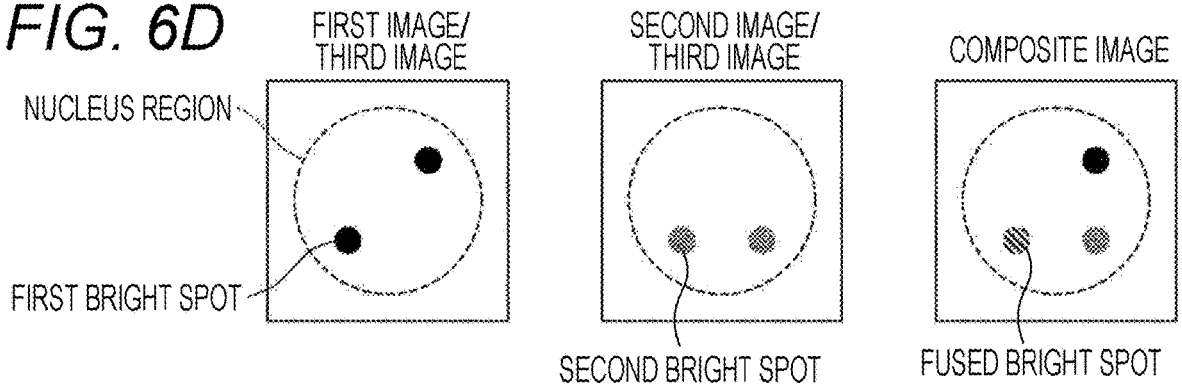

FIG. 7
A: ES PROBE
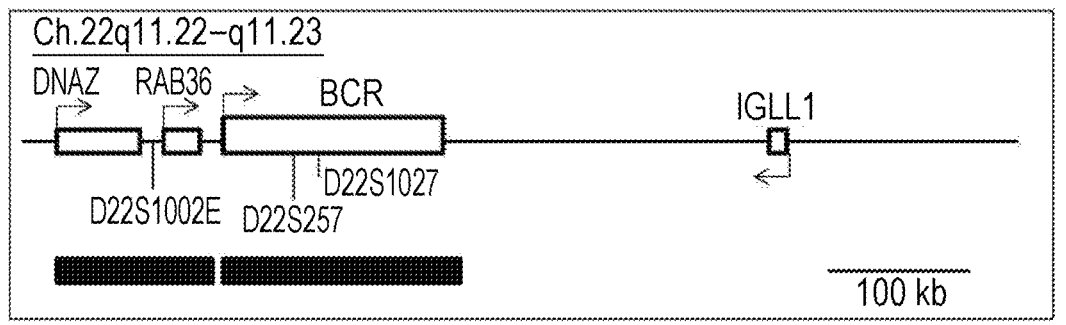
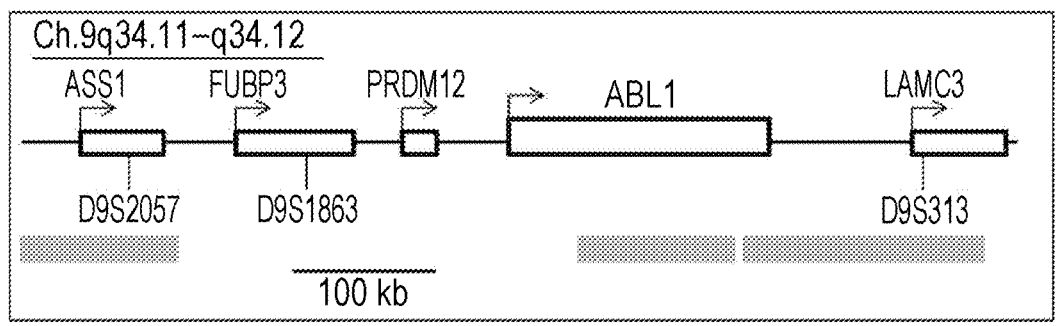
B: DF PROBE
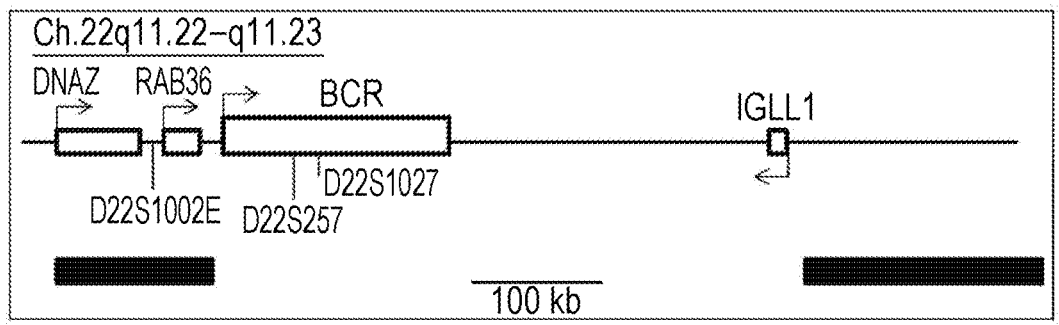
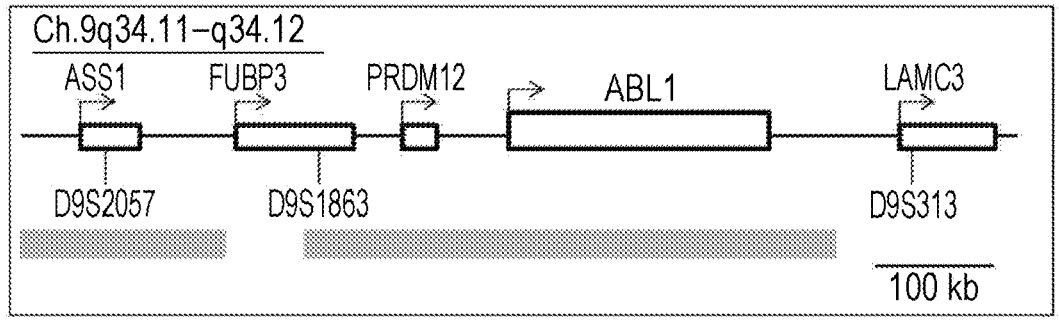

| MEASUREMENT ITEM | NAME OF PROBE | FIRST IMAGE | SECOND IMAGE | THIRD IMAGE | COMPOSITE IMAGE OF FIRST TO THIRD IMAGES | REFERENCE PATTERN | POSITIVITY/ NEGATIVITY OF CHROMOSOMAL ABNORMALITY |
|---|---|---|---|---|---|---|---|
| BCR/ABL FUSION GENE | ES | • •<br>• | ※<br>※ ※ | ◯ | ※<br>◦ • | FIRST BRIGHT SPOT: 1<br>SECOND BRIGHT SPOT: 1<br>FUSED BRIGHT SPOT: 2<br>(MINOR BCR/ABL PATTERN) | POSITIVE (ABNORMAL) |
| | ES | • • | ※<br>※ | ◯ | ※<br>◦ • | FIRST BRIGHT SPOT: 1<br>SECOND BRIGHT SPOT: 1<br>FUSED BRIGHT SPOT: 1<br>(CHROMOSOME 9 RECONFIGURATION: Ch. 9 OR 9q DELETION PATTERN) | POSITIVE (ABNORMAL) |
| | ES | • • | ※<br>※ | ◯ | ※<br>◦ • | FIRST BRIGHT SPOT: 1<br>SECOND BRIGHT SPOT: 1<br>FUSED BRIGHT SPOT: 1<br>(9q AND 22q DELETION PATTERN) | POSITIVE (ABNORMAL) |
| | DF | • •<br>• | ※<br>※ ※ | ◯ | ※<br>◦ • ◦ | FIRST BRIGHT SPOT: 1<br>SECOND BRIGHT SPOT: 1<br>FUSED BRIGHT SPOT: 2<br>(MINOR BCR/ABL PATTERN) | POSITIVE (ABNORMAL) |
| | DF | • •<br>• | ※ | ◯ | ※<br>• ◦ | FIRST BRIGHT SPOT: 2<br>SECOND BRIGHT SPOT: 1<br>FUSED BRIGHT SPOT: 1<br>(CHROMOSOME 9 RECONFIGURATION: Ch. 9 OR 9q DELETION PATTERN) | POSITIVE (ABNORMAL) |
| | DF | •<br>• | ※<br>※ | ◯ | ※<br>◦ • | FIRST BRIGHT SPOT: 1<br>SECOND BRIGHT SPOT: 1<br>FUSED BRIGHT SPOT: 1<br>(9q AND 22q DELETION PATTERN) | POSITIVE (ABNORMAL) |

• : FIRST BRIGHT SPOT    ※ : SECOND BRIGHT SPOT    ◦ : FUSED BRIGHT SPOT    ◯ : NUCLEUS REGION

FIG. 11

| MEASUREMENT ITEM | NAME OF PROBE | FIRST IMAGE | SECOND IMAGE | THIRD IMAGE | COMPOSITE IMAGE OF FIRST TO THIRD IMAGES | REFERENCE PATTERN | POSITIVITY/ NEGATIVITY OF CHROMOSOMAL ABNORMALITY |
|---|---|---|---|---|---|---|---|
| ALK GENE | ALK | ● ● | ※ ※ | ○ | ○ ○ | FIRST BRIGHT SPOT: 0<br>SECOND BRIGHT SPOT: 0<br>FUSED BRIGHT SPOT: 2 | NEGATIVE (NORMAL) |
| ALK GENE | ALK | ● ● | ※ ※ | ○ | ● ● | FIRST BRIGHT SPOT: 0<br>SECOND BRIGHT SPOT: 0<br>FUSED BRIGHT SPOT: 2 | NEGATIVE (NORMAL) |
| ALK GENE | ALK | ● ● | ※ ※ | ○ | ○ ● | FIRST BRIGHT SPOT: 1<br>SECOND BRIGHT SPOT: 1<br>FUSED BRIGHT SPOT: 1 | POSITIVE (ABNORMAL) |
| ALK GENE | ALK | ● ● | ※ ※ | ○ | ● ※ ● ※ | FIRST BRIGHT SPOT: 2<br>SECOND BRIGHT SPOT: 2<br>FUSED BRIGHT SPOT: 0 | POSITIVE (ABNORMAL) |
| LONG ARM DELETION OF CHROMOSOME 5 | 5q | ● ● | ※ ※ | ○ | ● ※ ● ※ | FIRST BRIGHT SPOT: 2<br>SECOND BRIGHT SPOT: 2<br>FUSED BRIGHT SPOT: 0 | NEGATIVE (NORMAL) |
| LONG ARM DELETION OF CHROMOSOME 5 | 5q | ● | ※ ※ | ○ | ● ※ ※ | FIRST BRIGHT SPOT: 1<br>SECOND BRIGHT SPOT: 2<br>FUSED BRIGHT SPOT: 0 | POSITIVE (ABNORMAL) |
| TRISOMY OF CHROMOSOME 8 | 17q | ●● ● | | ○ | ●● ● | FIRST BRIGHT SPOT: 3 | POSITIVE (ABNORMAL) |

● : FIRST BRIGHT SPOT    ※ : SECOND BRIGHT SPOT    ○ : FUSED BRIGHT SPOT    ( ) : NUCLEUS REGION

FIG. 12

| Specimen ID | Test Name | | | | | | | | | | | | |
|---|---|---|---|---|---|---|---|---|---|---|---|---|---|
| ▲ A01 | BCRABL ▼ | | | | | | | | | | | | |
| A02 | BCRABL DF | | | | | | | | | | | | |
| A03 | BCRABL ES | | | | | | | | | | | | |
| A04 | BCRABL ES | | | | | | | | | | | | |
| A05 | BCRABL ES | | | | | | | | | | | | |
| A06 | BCRABL ES | | | | | | | | | | | | |
| A07 | BCRABL ES | | | | | | | | | | | | |
| A08 | BCRABL ES | | | | | | | | | | | | |
| A09 | BCRABL ES | | | | | | | | | | | | |
| A10 | BCRABL ES | | | | | | | | | | | | |
| A11 | BCRABL ES | | | | | | | | | | | | |
| A12 | BCRABL ES | | | | | | | | | | | | |
| A13 | BCRABL ES | | | | | | | | | | | | |
| A14 | BCRABL ES | | | | | | | | | | | | |

[Run] [Cancel]

| All | 1 | 2 | 3 | 4 | 5 | 6 | 7 | 8 | 9 | 10 | 11 | 12 |
|---|---|---|---|---|---|---|---|---|---|---|---|---|
| A | ○ | ○ | ○ | ○ | ○ | ○ | ○ | ○ | ○ | ○ | ○ | ○ |
| B | ○ | ○ | ○ | ○ | ○ | ○ | ○ | ○ | ○ | ○ | ○ | ○ |
| C | ○ | ○ | ○ | ○ | ○ | ○ | ○ | ○ | ○ | ○ | ○ | ○ |
| D | ○ | ○ | ○ | ○ | ○ | ○ | ○ | ○ | ○ | ○ | ○ | ○ |
| E | ○ | ○ | ○ | ○ | ○ | ○ | ○ | ○ | ○ | ○ | ○ | ○ |
| F | ○ | ○ | ○ | ○ | ○ | ○ | ○ | ○ | ○ | ○ | ○ | ○ |
| G | ○ | ○ | ○ | ○ | ○ | ○ | ○ | ○ | ○ | ○ | ○ | ○ |
| H | ○ | ○ | ○ | ○ | ○ | ○ | ○ | ○ | ○ | ○ | ○ | ○ |

FIG. 13

FLUORESCENCE IMAGE ANALYZING APPARATUS, METHOD OF ANALYZING FLUORESCENCE IMAGE, AND COMPUTER PROGRAM

CROSS REFERENCE TO RELATED APPLICATIONS

This application is a continuation application of non-provisional U.S. patent application Ser. No. 15/951,562, filed on Apr. 12, 2018, which claims priority from prior Japanese Patent Application No. 2017-080855, filed on Apr. 14, 2017, entitled "FLUORESCENCE IMAGE ANALYZING APPARATUS, METHOD OF ANALYZING FLUORESCENCE IMAGE, AND COMPUTER PROGRAM", the entire contents of which are incorporated herein by reference.

TECHNICAL FIELD

The present invention relates to a fluorescence image analyzing apparatus, a method of analyzing a fluorescence image, and a computer program.

BACKGROUND

WO 2003/048300 discloses a method for treating cells when a flow cytometer or the like is applied for detection in a fluorescence in situ hybridization method (FISH method). In the FISH method, first, a pretreatment for hybridizing a fluorescently labeled probe to the base sequence of a target site present in the nucleus of a cell is performed to fluorescently label the target site. Subsequently, the fluorescence (bright spot) generated from the fluorescently labeled probe is detected. According to the FISH method, chromosomal abnormalities can be detected using a fluorescently labeled probe that binds to a target site on a chromosome even in a non-dividing cell. Furthermore, according to the FISH method, cells having chromosomal abnormalities coexisting with normal cells can be also detected, and the ratio thereof can be also analyzed.

Analysis by the FISH method is currently performed mainly by the eyes of a person (operator) using a fluorescence microscope. The operator must memorize a positive pattern for determining that there is an abnormality and a negative pattern for determining that there is no abnormality for each probe to be used in detection. However, currently there are dozens of probes for detecting chromosomal abnormalities by the FISH method, and among positive patterns, there are typical chromosomal abnormal patterns and non-typical chromosomal abnormal patterns. The operator has to know the positive pattern and the negative pattern for all of these, and the analysis by the FISH method has become complicated. Furthermore, since the judgment of a bright spot depends on the operator's sensation, criteria for determining whether a bright spot pattern of a fluorescent dye of an observed cell is a positive pattern or a negative pattern changes depending on the skill of the operator, and it is difficult to maintain the accuracy of judgment of the presence or absence of a chromosomal abnormality by the FISH method.

SUMMARY OF THE INVENTION

The scope of the present invention is defined solely by the appended claims, and is not affected to any degree by the statements within this summary.

A first aspect of the present invention relates to a fluorescence image analyzing apparatus. A fluorescence image analyzing apparatus (1) according to this aspect includes a light source (120 to 123) that emits light to a sample (10) including a plurality of cells labeled with a fluorescent dye at a target site, an imaging unit (160) that captures that captures a fluorescence image of each of the cells that emit fluorescence by being irradiated with the light, and a processing unit (11) that processes the fluorescence image captured by the imaging unit (160) to acquire a bright spot pattern of fluorescence in the fluorescence image. The processing unit (11) selects a reference pattern corresponding to a measurement item of the sample (10) from a plurality of reference patterns corresponding to a plurality of measurement items and generates information used for determination of the sample (10) based on the bright spot pattern of fluorescence in the fluorescence image and the selected reference pattern.

A second aspect of the present invention relates to a method of analyzing a fluorescence image in which a fluorescence image of a cell obtained by imaging a sample (10) including a plurality of cells in which a target site is labeled with a fluorescent dye is analyzed. In the analysis method according to this aspect, a measurement item of the sample (10) is received, a reference pattern corresponding to the received measurement item of the sample (10) is read from a plurality of reference patterns corresponding to a plurality of measurement items, information used for determination of the sample (10) is generated based on a bright spot pattern of fluorescence in the fluorescence image and the read reference pattern, and the generated information used for determination of the sample (10) is displayed.

A third aspect of the present invention relates to computer program for causing a computer to execute an analysis process of a fluorescence image of a cell obtained by imaging a sample (10) including a plurality of cells in which a target site is labeled with a fluorescent dye is analyzed. The computer program according to this aspect causes the computer to execute steps of receiving a measurement item of the sample (10), reading a reference pattern corresponding to the received measurement item of the sample (10) from a plurality of reference patterns corresponding to a plurality of measurement items, generating information used for determination of the sample (10) based on a bright spot pattern of fluorescence in the fluorescence image and the read reference pattern, and displaying the generated information used for determination of the sample (10).

According to the first to third aspects of the present invention, information used for determination of the sample is generated and displayed based on the bright spot pattern of fluorescence in a fluorescence image acquired for each cell and a reference pattern corresponding to the measurement item of the sample among reference patterns corresponding to a plurality of measurement items. Therefore, it is unnecessary for an operator or the like to memorize many kinds of bright spot patterns indicating abnormal cells having chromosomal abnormalities to determine whether a cell is an abnormal cell, and the determination of abnormal cell does not depend on the sensation of the operator. Therefore, the determination accuracy of abnormal cells can be improved, and as a result, the accuracy of the information used for determination of the sample can be improved.

BRIEF DESCRIPTION OF THE DRAWINGS

FIG. 3 is a flowchart for describing an operation of a processing unit;

FIGS. 6A to 6D are respectively schematic diagrams for describing bright spot patterns of a negative pattern and positive patterns 1 to 3;

FIG. 7 is a diagram showing an example of a target site to which each probe targeted to a BCR/ABL fusion gene hybridizes;

FIG. 8 is a diagram showing examples of reference patterns of typical positive patterns of a BCR/ABL fusion gene;

FIG. 9 is a diagram showing examples of reference patterns of non-typical positive patterns of a BCR/ABL fusion gene;

FIG. 11 is a diagram showing examples of a reference pattern of a negative pattern and a positive pattern and an example of a chromosomal abnormality in which a long arm of chromosome 5 (5q) is deleted when a chromosomal abnormality associated with an ALK locus is detected;

FIG. 12 shows an example of a display screen of a display unit of the fluorescence image analyzing apparatus;

FIG. 13 shows an example of a display screen of the display unit of the fluorescence image analyzing apparatus;

DETAILED DESCRIPTION OF THE PREFERRED EMBODIMENTS

Hereinafter, embodiments of the present disclosure will be described in detail with reference to attached drawings. In the following embodiment, the present disclosure is applied to an apparatus and a method in which a sample subjected to a pretreatment of hybridizing a target site (target sequence) present in the nucleus of a cell with a nucleic acid probe (hereinafter simply referred to as a probe) including a nucleic acid sequence having a sequence complementary to the target sequence and labeled with a fluorescent dye is measured and a fluorescence image acquired for each cell among a plurality of cells in the sample is analyzed.

Figure 8:
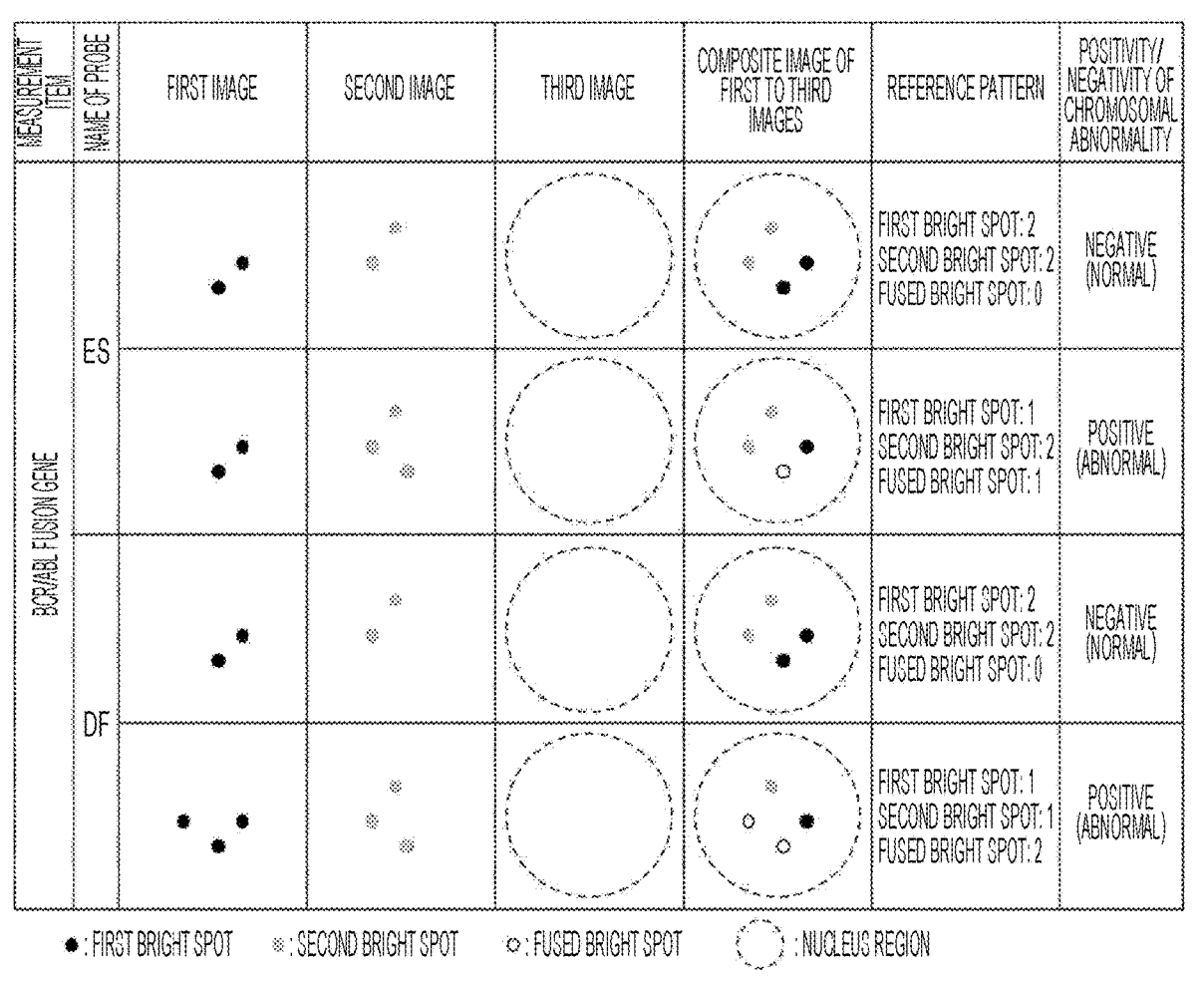

In one example of this embodiment, analysis of chromosomal abnormalities by a fluorescence in situ hybridization (FISH) method is performed by, for example, a flow cytometer (e.g., imaging flow cytometer), a fluorescence microscope, or the like. In the following embodiment, as an example, an embodiment in which a BCR gene on chromosome 22 and an ABL gene on chromosome 9 are set as target sites in a nucleic acid, and cells having a translocation (a BCR/ABL fusion gene, also referred to as a Philadelphia chromosome: t (9; 22) (q34.12; q11.23)) between chromosome 9 and chromosome 22 observed in chronic myelogenous leukemia are measured and analyzed will be described. Chromosomal abnormalities detected by the fluorescence image analyzing apparatus are not limited as long as the abnormalities can be detected by the FISH method. Examples of chromosomal abnormalities include translocations, deletions, inversions, and duplications. Specific examples of the chromosomal abnormalities include chromosomal abnormalities associated with loci such as BCR/ABL fusion gene and ALK gene. FIGS. 8, 9, and 11 show a positive pattern for each gene for determining that there is a chromosomal abnormality.

In the following embodiment, cells to be measured are not limited as long as the cells are nucleated cells. For example, the cells may be nucleated cells in a specimen collected from a subject, and may be preferably nucleated cells in a blood specimen. In this specification and the like, the sample is a cell suspension to be subjected to measurement including cells derived from a specimen including a target site hybridized with a probe. The sample includes a plurality of cells. The number of the plurality of cells are at least $10^2$ or more, preferably $10^3$ or more, more preferably $10^4$ or more, further preferably $10^5$ or more, and still more preferably $10^6$ or more.

In this embodiment, an abnormal cell refers to a cell having a chromosomal abnormality. Examples of abnormal cells include tumor cells such as cancer cells. Preferable examples of abnormal cells include hematopoietic tumor cell such as leukemia and cancer cells such as lung cancer.

Figure 1:
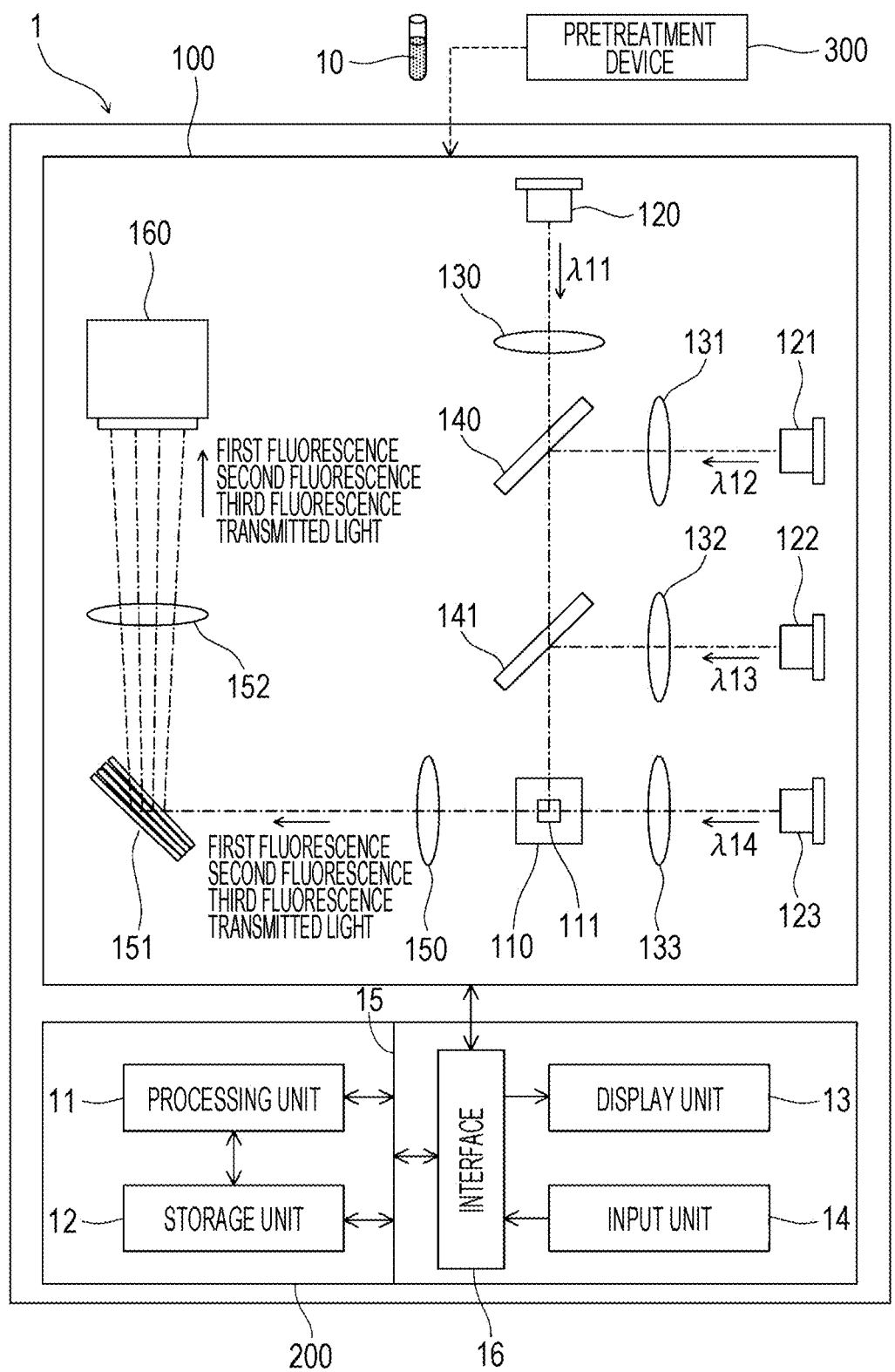
FIG. 1 is a schematic diagram showing a configuration of an embodiment of a fluorescence image analyzing apparatus.

FIG. 1 shows a schematic configuration of a fluorescence image analyzing apparatus 1 of this embodiment. The fluorescence image analyzing apparatus 1 shown in FIG. 1 includes a measurement device 100 and a processing device 200, and measures and analyzes a sample 10 prepared by a pretreatment by a pretreatment device 300. An operator collects nucleated cells that are measurement target cells by, for example, centrifugally separating a blood specimen, collected from a subject, by using a cell separation medium such as Ficoll. In collecting the nucleated cells, the nucleated cells may be collected by hemolyzing erythrocytes or the like by using a hemolyzing agent to leave nucleated cells instead of collecting the nucleated cells by centrifugation. The pretreatment device 300 includes a mixing container for mixing the nucleated cell suspension acquired by centrifugation or the like with a reagent, a dispensing unit for dispensing the nucleated cell suspension and reagent to the mixing container, a heating unit for heating the mixing container, and the like. The pretreatment device 300 performs a pretreatment including a step of labeling a target site in a cell collected from a subject with a fluorescent dye and a step of staining the nucleus of the cell with a nuclear dye, and thus prepares a sample 10. Specifically, in the step of labeling a target site with a fluorescent dye, the target sequence and a probe including a nucleic acid sequence having a sequence complementary to the target sequence and labeled with a fluorescent dye are hybridized.

In the FISH method, a target site on a chromosome is detected by using one or more fluorescent dyes. Preferably, in the FISH method, two or more fluorescent dyes are used to detect a target site on a first chromosome and a target site on a second chromosome ("first" or "second" is a concept of a comprehensive number and does not indicate a chromosome number). For example, a probe that hybridizes with a BCR locus is a nucleic acid having a sequence complementary to the base sequence of the BCR locus and is labeled with a first fluorescent dye that generates a first fluorescence of a wavelength $\lambda 21$ by being irradiated with light of a wavelength $\lambda 11$. By using this probe, the BCR locus is labeled with the first fluorescent dye. A probe that hybridizes with an ABL locus is a nucleic acid having a sequence complementary to the base sequence of the ABL locus and is labeled with a second fluorescent dye that generates a second fluorescence of a wavelength $\lambda 22$ by being irradiated with light of a wavelength $\lambda 12$. By using this probe, the ABL locus is labeled with the second fluorescent dye. The nucleus is stained with a nuclear dye that generates a third fluorescence of a wavelength of $\lambda 23$ by being irradiated with light of a wavelength $\lambda 13$. The light of wavelength $\lambda 11$, the light of wavelength $\lambda 12$, and the light of wavelength $\lambda 13$ are so-called excitation light.

More specifically, the pretreatment device 300 performs a treatment for immobilizing cells so that the cells do not contract due to dehydration, a membrane permeation treatment of opening a hole having a size through which a probe can be introduced into a cell, a heat modification treatment of applying heat to cells, a treatment of hybridizing the target site and the probe, a washing treatment of removing unnecessary probes from the cells, and a treatment of staining the nucleus.

The measurement device 100 includes a flow cell 110, light sources 120 to 123, condenser lenses 130 to 133, dichroic mirrors 140 and 141, a condenser lens 150, an optical unit 151, a condenser lens 152, and an imaging unit 160. The sample 10 is flowed through a flow channel 111 of the flow cell 110.

The light sources 120 to 123 irradiate the sample 10 flowing through the flow cell 110 with light. The light sources 120 to 123 are constituted by, for example, semiconductor laser light sources. Light of wavelengths $\lambda 11$ to $\lambda 14$ is respectively emitted from the light sources 120 to 123.

The condenser lenses 130 to 133 respectively collect light of wavelengths $\lambda 11$ to $\lambda 14$ emitted from the light sources 120 to 123, respectively. The dichroic mirror 140 transmits light of wavelength $\lambda 11$ and refracts light of wavelength $\lambda 12$. The dichroic mirror 141 transmits light of wavelengths $\lambda 11$ and $\lambda 12$ and refracts light of wavelength $\lambda 13$. In this manner, the sample 10 flowing through the flow channel 111 of the flow cell 110 is irradiated with the light of wavelengths $\lambda 11$ to $\lambda 14$. The number of semiconductor laser light sources provided in the measurement device 100 is not limited as long as 1 or more light sources are provided. The number of semiconductor laser light sources can be selected from among, for example, 1, 2, 3, 4, 5 and 6.

When the sample 10 flowing through the flow cell 110 is irradiated with light of wavelengths $\lambda 11$ to $\lambda 13$, fluorescence is generated from the fluorescent dye staining the cells. Specifically, when the first fluorescent dye labeling the BCR locus is irradiated with the light of wavelength $\lambda 11$, first fluorescence of wavelength $\lambda 21$ is generated from the first fluorescent dye. When the second fluorescent dye labeling the ABL locus is irradiated with the light of wavelength $\lambda 12$, second fluorescence of wavelength $\lambda 22$ is generated from the second fluorescent dye. When the nuclear dye staining the nucleus is irradiated with the light of wavelength $\lambda 13$, third fluorescence of wavelength $\lambda 23$ is generated from the nuclear dye. When the sample 10 flowing through the flow cell 110 is irradiated with the light of wavelength $\lambda 14$, this light transmits through the cells. The transmitted light of wavelength $\lambda 14$ that has been transmitted through the cells is used for generating a bright field image. For example, in the embodiment, the first fluorescence is in a wavelength band of green light, the second fluorescence is in a wavelength band of red light, and the third fluorescence is in a wavelength band of blue light.

The condenser lens 150 collects the first to third fluorescence generated from the sample 10 flowing through the flow channel 111 of the flow cell 110 and the transmitted light transmitted through the sample 10 flowing through the flow channel 111 of the flow cell 110. The optical unit 151 has a configuration in which four dichroic mirrors are combined. The four dichroic mirrors of the optical unit 151 reflect the first to third fluorescence and the transmitted light at slightly different angles from each other and separate the light on a light receiving surface of the imaging unit 160. The condenser lens 152 condenses the first to third fluorescence and the transmitted light.

The imaging unit 160 is constituted by a time delay integration (TDI) camera. The imaging unit 160 images the first to third fluorescence and the transmitted light and outputs fluorescence images respectively corresponding to the first to third fluorescence and a bright field image corresponding to the transmitted light as imaging signals to the processing device 200. The fluorescence images corresponding to the first to third fluorescence are hereinafter respectively referred to as a "first image", a "second image", and a "third image". The "first image", "second image" and "third image" preferably have the same size in order to analyze overlapping of bright spots. The "first image", "second image", and "third image" may be color images or gray scale images.

Figure 2A:
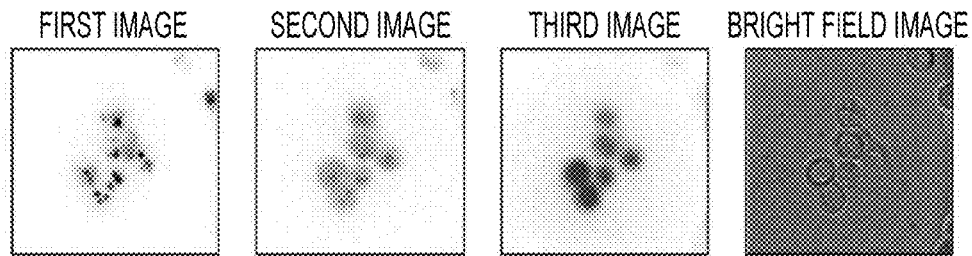
FIG. 2A is a diagram exemplifying first to third images and a bright field image acquired by the fluorescence image analyzing apparatus.

FIG. 2A shows examples of fluorescence images. In the first image of FIG. 2A, a portion that looks like a dark dot shows a bright spot of the first fluorescence, that is, a target site labeled with the first fluorescent dye. In the second image, although not as vivid as in the first image, a dark gray dot is observed in a light gray color indicating a nucleus. This indicates a bright spot of the second fluorescence, that is, a target site labeled with the second fluorescent dye. In the third image, a region of a substantially circular nucleus is represented in black. In a bright field image, the state of actual cells can be observed. Each image in FIG. 2A is an image showing an example in which white blood cells after a pretreatment are placed on a glass slide and observed under a microscope, and, in raw data of the fluorescence image, brighter spots indicate higher fluorescence intensity and darker spots indicate lower fluorescence intensity. In the first to third images in FIG. 2A, the gradation of the imaged raw data is reversed and represented in gray scale. In the case where the sample 10 flowing through the flow cell 110 is imaged by the imaging unit 160 as described above, since the cells flow through the flow channel 111 in a state of being separated from each other, the fluorescence image and the bright field image are acquired for each cell.

Returning to FIG. 1, the processing device 200 includes a processing unit 11, a storage unit 12, a display unit 13, and an input unit 14 as a hardware configuration. The processing unit 11 is constituted by a processor (central processing unit: CPU). The storage unit 12 is constituted by a readable and writable memory (random access memory: RAM) used as a work area for various processes of the processing unit 11, a read-only memory (ROM) for storing computer programs and data, a hard disk, and the like. The processing unit 11 and the storage unit 12 can be configured by a general-purpose computer. The hard disk may be included in the computer or may be placed as an external device of the computer. The display unit 13 is constituted by a display. The input unit 14 is constituted by a mouse, a keyboard, a touch panel device, or the like. The processing unit 11 transmits data to and from the storage unit 12 via a bus 15, and inputs and outputs data to and from the display unit 13, the input unit 14, and the measurement device 100 via an interface 16.

The processing unit 11 reads out various computer programs stored in the ROM or the hard disk to the RAM, executes the computer programs, and thus processes the fluorescence image of cells obtained by the measurement of the sample 10 performed by the measurement device 100, and controls operations of the display unit 13, the input unit 14, and the like. Specifically, the processing unit 11 processes the fluorescence image to acquire a bright spot pattern of the fluorescence in the fluorescence image, and selects, from a plurality of reference patterns corresponding to a plurality of measurement items stored in the storage unit 12, a reference pattern corresponding to a measurement item of the sample 10. Then, based on the bright spot pattern of fluorescence in the fluorescence image and the selected reference pattern, information used for determination of the sample 10 is generated.

Hereinafter, an example of a method of analyzing a fluorescence image performed by the processing unit 11 based on a computer program defining a processing procedure for analyzing a fluorescence image of a cell will be described with reference to FIGS. 3 to 5. The computer program is stored in the storage unit 12 in advance, but may be installed from a computer-readable portable recording medium (not shown) such as a CD-ROM, or, for example, may be installed by being downloaded from an external server via a network (not shown).

Figure 4:
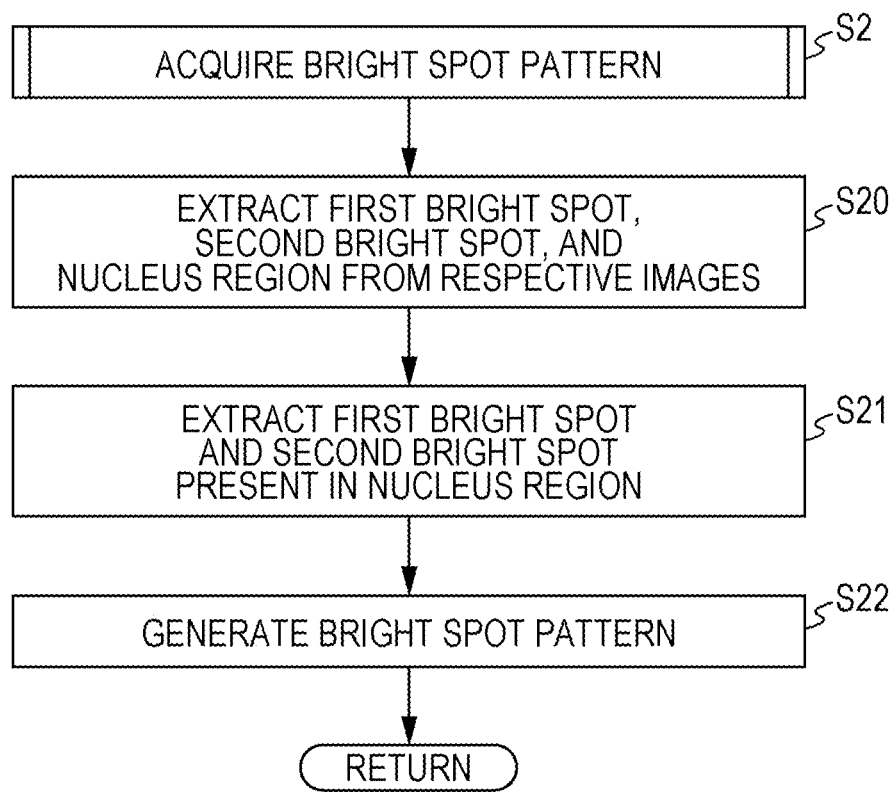
FIG. 4 is a flowchart for describing an operation of the processing unit.
Figure 5:
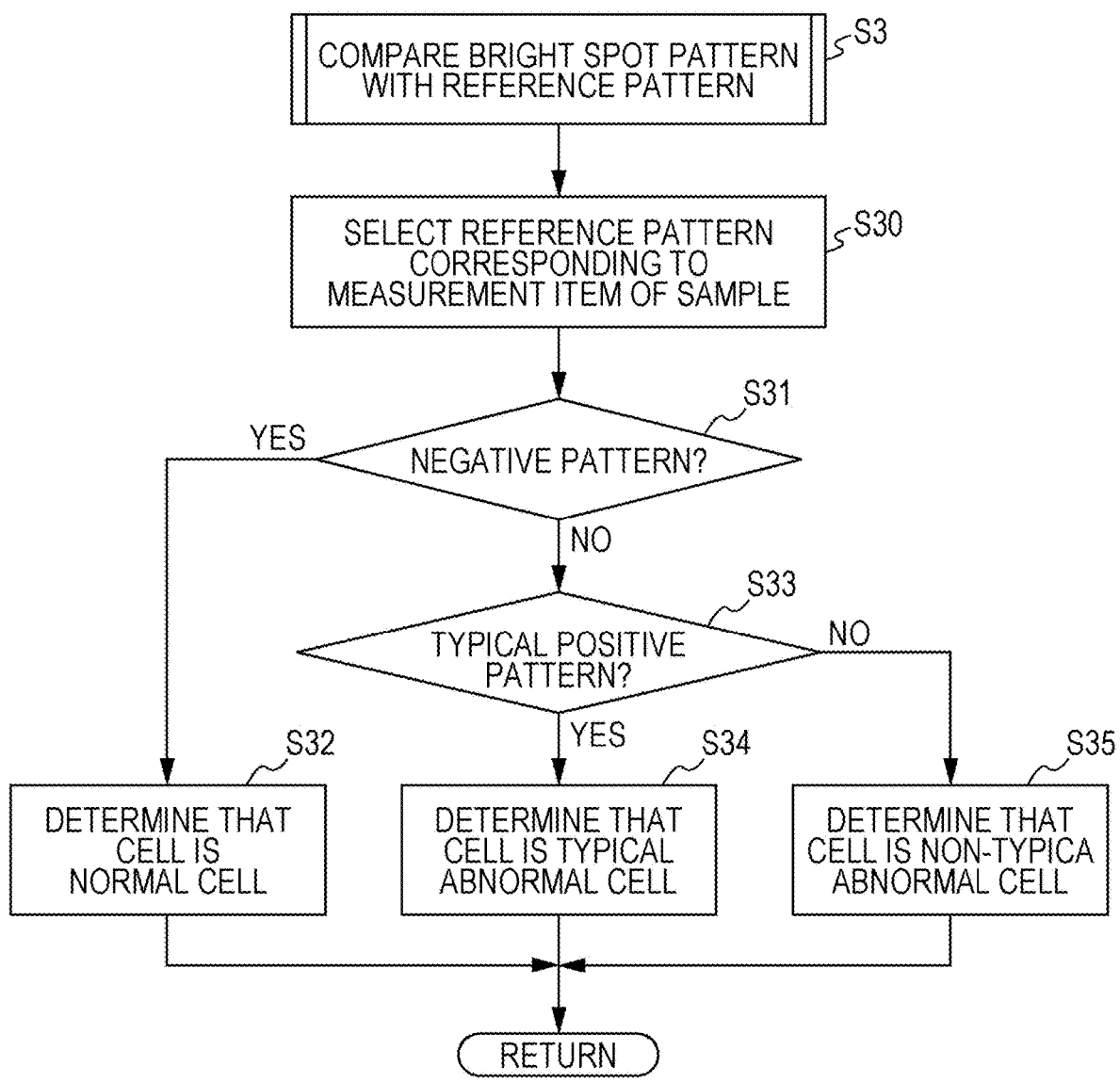
FIG. 5 is a flowchart for describing an operation of the processing unit.

As shown in FIGS. 3 to 5, the processing unit 11 performs respective processes in an image acquisition step S1, a bright spot pattern acquisition step S2, a comparison step S3 of a bright spot pattern and a reference pattern, a display step S4 of a determination result of whether a cell is an abnormal cell or a normal cell, a generation step S5 of information used for determination of the sample, and a display step S6 of the information used for determination of the sample.

First, in step S1, the processing unit 11 acquires the first to third images displayed in grayscale by gradation inversion of the raw data captured by the imaging unit 160. The processing unit 11 causes the storage unit 12 to store the acquired first to third images.

Next, in step S2, the processing unit 11 acquires a bright spot pattern of the first fluorescence in the first image based on the first fluorescence and acquires a bright spot pattern of the second fluorescence in the second image based on the second fluorescence.

In this step S2, as shown in FIG. 4, in step S20, the processing unit 11 firstly extracts bright spots (first bright spots) of the first fluorescence, second bright spots (second bright spot) of the second fluorescence, and a nucleus region from each the first image, the second image, and the third image. More specifically, referring to FIGS. 2B to 2D, the third image shown at the left end of FIG. 2B, the first image shown at the left end of FIG. 2C, and the second image shown at the left end of FIG. 2D are acquired from one cell flowing through the flow cell 110.

Figure 2B:
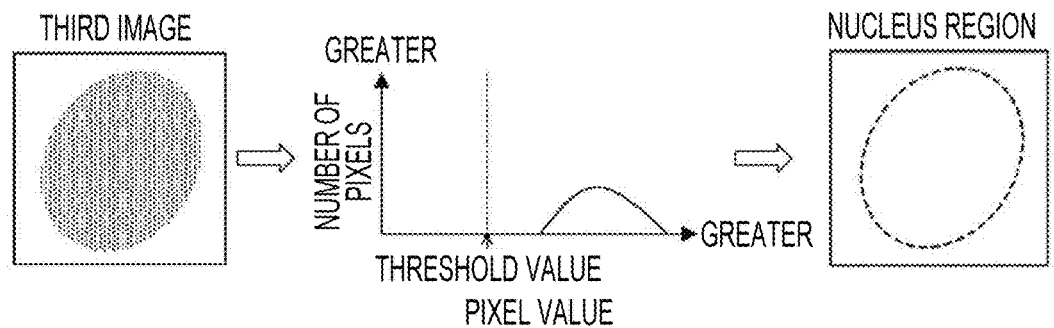
FIG. 2B is a schematic diagram for describing extraction of a nucleus region performed by the fluorescence image analyzing apparatus.

When a third image as shown at the left end of FIG. 2B is acquired, the processing unit 11 firstly generates a graph of pixel values and number of pixels based on the pixel value of each pixel in horizontal (x direction) m×vertical (y direction) n pixels constituting the third image as shown in the center of FIG. 2B. The "number of pixels" of the vertical axis indicates the number of pixels. The number of pixels of the image is not particularly limited, is, for example, horizontal 51×vertical 51. The spatial resolution per pixel is also not particularly limited. Then, the processing unit 11 sets a threshold value of the pixel value in the graph of FIG. 2B, and extracts a range where pixels having pixel values larger than the threshold value as a nucleus region as indicated by a broken line at the right end of FIG. 2B.

Figure 2C:
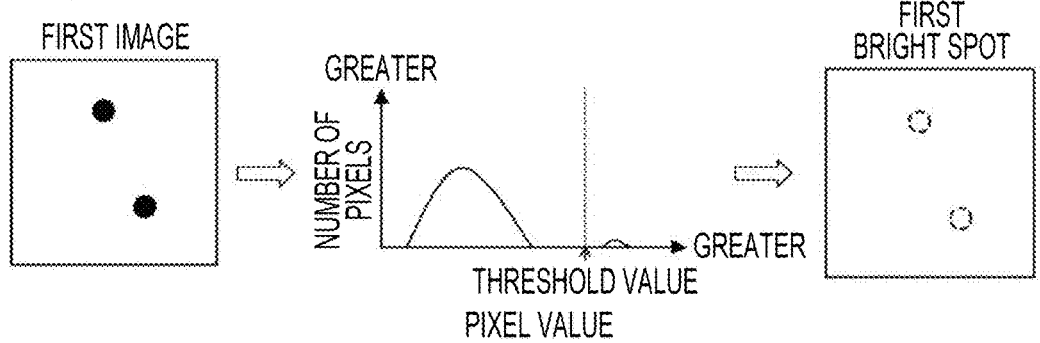
FIG. 2C and FIG. 2D are schematic diagrams for describing extraction of bright spots performed by the fluorescence image analyzing apparatus.

When a first image as shown at the left end of FIG. 2C is acquired, the processing unit 11 firstly generates a graph of pixel values and number of pixels based on the pixel value of each pixel in horizontal (x direction) m×vertical (y direction) n pixels constituting the first image as shown in the center of FIG. 2C. Then, the processing unit 11 sets a threshold value of the pixel value in the graph of FIG. 2C, for example, as a boundary between a bright spot and the background based on an Otsu method, and extracts a range where pixels having pixel values larger than the threshold value as a bright spot as indicated by a broken line at the right end of FIG. 2C. When extracting a bright spot from the first image, a bright spot having an extremely small range and a bright spot having an extremely large range are excluded.

Figure 2D:
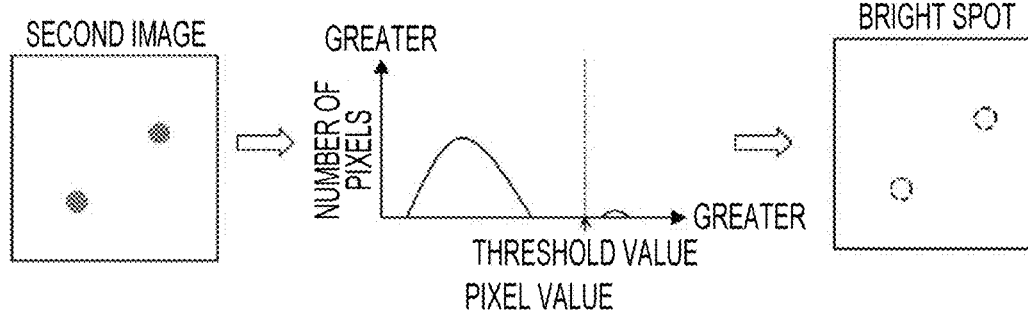

When a second image as shown at the left end of FIG. 2D is acquired, the processing unit 11 generates a graph of pixel values and number of pixels based on the pixel value of each pixel in horizontal (x direction) m×vertical (y direction) n pixels constituting the second image as shown in the center of FIG. 2D, similarly to the case of the first image. Then, the processing unit 11 sets a threshold value of the pixel value in the graph of FIG. 2D, and extracts a range where pixels having pixel values larger than the threshold value as a bright spot as indicated by a broken line at the right end of FIG. 2D. When extracting a bright spot from the second image, a bright spot having an extremely small range and a bright spot having an extremely large range are excluded.

Next, in step S21 of FIG. 4, the processing unit 11 compares the position of the nucleus region extracted from the third image with the position of the bright spot extracted from the first image, and excludes a bright spot that is not included in the nucleus region. As a result, first bright spots of the first fluorescence are extracted from the first image, and the number and positions of the first bright spots in the first image are derived. Similarly, the processing unit 11 compares the position of the nucleus region extracted from the third image with the position of the bright spot extracted from the second image, and excludes a bright spot that is not included in the nucleus region. As a result, second bright spots of the second fluorescence are extracted from the second image, and the number and positions of the second bright spots in the second image are derived.

The positions of the nucleus region and the bright spots in each image can be measured by, for example, determining coordinate information (x, y) for horizontal (x direction) m×vertical (y direction) n pixels constituting each image and based on the coordinate information of a plurality of pixels included in the nucleus region and bright spots.

The processing unit 11 may extract a nucleus region from the third image and bright spots from the first image and the second image by calculation according to the above procedure without generating the graphs as shown in the center of FIGS. 2B to 2D. The extraction of the bright spots may be performed by determining the degree of matching between a distribution waveform of normal bright spots and a target region of determination and extracting the target region of determination as a bright spot when the degree of matching is high. Although the processing unit 11 detects cells by extracting the nucleus region from the third image in the description above, the processing unit 11 may detect the cells based on a bright field image. In the case where cells are detected based on the bright field image, acquisition of the third image may be omitted. A bright spot in the present embodiment refers to a point of small fluorescence generated in the fluorescence image. More specifically, the bright spot refers to the central point of a bright spot (the position of the pixel having the greatest pixel value (fluorescence intensity)). The extraction of the bright spots can be performed by, for example, converting the color gradation of pixels other than the pixels designated as bright spots to the same level as the background.

A "pixel value" in this specification refers to a digital value assigned to each pixel of an image, and in particular, in an output image (so-called raw image) from a camera, refers to a value of the luminance of an imaging target object converted into a digital signal.

Next, in step S22, based on an arrangement example (number and positions) of the first bright spots and the second bright spots extracted from the first image and the second image, the processing unit 11 extracts first bright spots and second bright spots overlapping each other in a composite image of the first image and the second image.

First, a method of determining whether or not a cell is an abnormal cell having a chromosomal abnormality will be described.

FIG. 6A shows an arrangement example of bright spots of a normal cell having no chromosomal abnormality, that is, an example of bright spot pattern (negative pattern), and FIGS. 6B to 6D show examples of bright spot patterns (positive patterns) of abnormal cells. In any of FIGS. 6A to 6D, each image is shown in a state of being superimposed with the third image.

As shown in FIG. 6A, when there is no chromosomal abnormality such as translocation of BCR locus and ABL locus, each gene exists as one pair in one nucleus, and each allele independently exists. Therefore, in the first image, there are two first bright spots in one nucleus region. In the second image, there are two second bright spots in one nucleus region. In this case, if the first image and the second image imaged at the same size are superimposed and combined, in the composite image, the two first bright spots and the two second bright spots are present without overlapping in one nucleus region. Therefore, a cell in which two first bright spots and two second bright spots are present in the nucleus region as shown in FIG. 6A is determined to be a normal cell in which no chromosomal abnormality is observed, that is, the chromosome abnormality is negative.

An example of a positive pattern will be described by using a case where a probe targeting a BCR/ABL fusion gene [Cytocell BCR/ABL Translocation, Extra Signal (ES) Probe (Sysmex Corporation)] (hereinafter sometimes simply referred to as an "ES probe") as an example. There are several kinds of probes targeting BCR/ABL fusion genes. Examples of a target site to which each probe hybridizes are shown in FIG. 7. The BCR gene is located on chromosome 22q11.22-q11.23 and a probe hybridizing to the BCR locus is labeled with the first fluorescence (e.g., green). The ABL gene is located on chromosome 9q34.11-q34.12 and a probe that hybridizes to the ABL locus is labeled with the second fluorescence (e.g., red). FIG. 7A shows a binding site of the above-described ES probe, and FIG. 7B shows a binding site of a Cytocell BCR/ABL Translocation, Dual Fusion (DF) Probe (Sysmex Corporation, Cat No. LPH 007) (hereinafter simply referred to as "DF probe").

As shown in FIG. 6B, when a part of the ABL locus has moved to chromosome 9 due to translocation, there are two first bright spots in the nucleus in the first image, and there are three second bright spots in the nucleus in the second image. In this case, when combining the first image and the second image, in the composite image, one first bright spot, two second bright spots, and a bright spot (fused bright spot) of fourth fluorescence (for example, yellow) in which a first bright spot and a second bright spot overlap each other are present in one nucleus. Therefore, as shown in FIG. 6B, a cell in which the respective bright spots are present is determined to be an abnormal cell in which translocation occurs in the BCR locus and the ABL locus, that is, chromosomal abnormality is positive.

As shown in FIG. 6C, when a part of the BCR locus has moved to chromosome 22 due to translocation and a part of the ABL locus has moved to the chromosome 9, there are three first bright spots in the nucleus in the first image, and there are three second bright spots in the nucleus in the second image. In this case, when combining the first image and the second image, in the composite image, one first bright spot, one second bright spots, and two fused bright spots in which first bright spots and second bright spots overlap each other are present in one nucleus. Therefore, as shown in FIG. 6C, a cell in which the respective bright spots are present is determined to be an abnormal cell in which translocation occurs in the BCR locus and the ABL locus, that is, chromosomal abnormality is positive.

As shown in FIG. 6D, when a part of the ABL locus has moved to chromosome 9 due to translocation, there are two first bright spots in the nucleus in the first image, and there are two second bright spots in the nucleus in the second image. In this case, when combining the first image and the second image, in the composite image, one first bright spot, one second bright spots, and one fused bright spot in which a first bright spot and a second bright spot overlap each other are present in one nucleus. Therefore, as shown in FIG. 6D, a cell in which the respective bright spots are present is determined to be an abnormal cell in which translocation occurs in the BCR locus and the ABL locus, that is, chromosomal abnormality is positive.

As described above, it is possible to determine whether or not each cell is an abnormal cell having a chromosomal abnormality based on the positions and the number of the respective bright spots in the composite image obtained by combining the first image and the second image. Therefore, in step S22 of FIG. 4, the processing unit 11 counts, for each cell, as a bright spot pattern, the number of positions of the respective bright spots in the composite image of the first image and the second image, that is, the number of first bright spots at positions not overlapping the second bright spots, the number of second bright spots at positions not overlapping the first bright spots, and fused bright spots at positions where the first bright spots and the second bright spots overlap. For example, in FIG. 6D, the bright spot pattern may be generated by setting the number of individual first bright spots to "1", the number of individual second bright spots to "1", and the number of fused bright spots constituted by first bright spots and second bright spots to "1".

A bright spot pattern and a reference pattern to be described later may be generated by indicating the first bright spot, the second bright spot, and the fused bright spot by colors. For example, it is possible to express an individual first bright spot by green (G), an individual second bright spot by red (R), and a fused bright spot by yellow (F), and a bright spot pattern can be generated by indicating the number of bright spots of G, R, and F respectively immediately after G, R, and F. For example, in FIG. 6D, the bright spot pattern can be displayed as "G1R1F1".

As a bright spot pattern of fluorescence of a fluorescence image may be generated by setting the total number of the first bright spots in the first image as the number of the first bright spots mentioned above, and setting the total number of the second bright spots in the second image as the number of the second bright spots mentioned above. For example, in FIG. 6D, the bright spot pattern can be generated by setting the number of first bright spots in the first image to "2", the number of second bright spots in the second image to "2", and the number of fused bright spots where first bright spots and second bright spots overlap each other and displayed as "G2R2F1", and this means the same thing.

Whether or not a first bright spot of the first image and a second bright spot of the second image overlap each other in the composite image can be determined from whether or not the ratio of a region in which the first bright spot and the second bright spot overlap each other, for example, the ratio of pixels at the same positions (coordinate information (x, y)) as pixels included in the second bright spot among a plurality of pixels included in the first bright spot is larger than a threshold value. This can be also determined based on whether or not the distance between the center point of the first bright spot (the position of the pixel having the highest fluorescence intensity) and the center point of the second bright spot (the position of the pixel having the highest fluorescence intensity) is smaller than a threshold value.

The bright spot pattern of fluorescence in the fluorescence image acquired for each cell may be the number of bright spots per color in the composite image. That is, instead of displaying each image in gray scale, the color of each pixel of the first image is displayed in green color gradation (RGB value) based on the pixel value, and the color of each pixel of the second image is displayed in red color gradation (RGB value). When the images are superimposed and combined, if the cell is an abnormal cell, based on the combination of the RGB values of each pixel of the composite image, the first bright spot of green, the second bright spot of red, and the fused bright spot of yellow are present in the nucleus region. Therefore, whether or not the cell is an abnormal cell can be determined by counting the number of bright spots for each color as a bright spot pattern.

The processing unit 11 causes the storage unit 12 to store the composite image of the first image and the second image generated in step S2 of FIG. 3 and the bright spot pattern of fluorescence in the composite image for each cell.

As described above, when acquiring the bright spot pattern of fluorescence in a fluorescence image of a cell, the processing unit 11 then determines whether the cell is an abnormal cell or a normal cell based on the bright spot pattern acquired for each cell. In this embodiment, the storage unit 12 stores reference patterns for determining whether the cell is an abnormal cell or a normal cell for each of a plurality of measurement items. In step S3, the processing unit 11 compares the bright spot pattern acquired for each cell with a reference pattern corresponding to the measurement item of the sample 10 among the plurality of reference patterns stored in the storage unit 12, and thus determines, for each cell, whether or not the cell is an abnormal cell. The determination of abnormal cell by the processing unit 11 will be described later with reference to FIG. 5.

The reference pattern includes at least one of a bright spot pattern (positive pattern) of fluorescence in a fluorescence image of an abnormal cell having a chromosomal abnormality and a bright spot pattern (negative pattern) of fluorescence in a fluorescence image of a normal cell having no chromosomal abnormality, for example, as shown in FIGS. 6A to 6D. In this embodiment, the reference pattern includes both of the bright spot pattern (positive pattern) of an abnormal cell and the bright spot pattern (negative pattern) of a normal cell.

In this embodiment, as shown in, for example, FIGS. 8, 9 and 11, BCR/ABL fusion gene, ALK gene, reference pattern of long arm deletion of chromosome 5 (negative pattern and positive pattern) are stored as measurement items in the storage unit 12. Further, in this embodiment, the measurement items are further classified by probes that hybridize to the target site, and the reference pattern is stored for each probe in the storage unit 12. Furthermore, in this embodiment, a reference pattern (positive pattern) of an abnormal cell is stored in the storage unit 12 by being classified into a reference pattern of a typical abnormal cell (a typical positive pattern) and a reference pattern of a non-typical abnormal cell (a non-typical positive pattern) for each probe.

FIG. 8 shows examples of a reference pattern of a typical positive pattern (major pattern) of BCR/ABL fusion gene. In the state in which the first image and the second image are superimposed, when the ES probe is used, the number of the first bright spots is two, the number of the second bright spots is two, and the number of the fused bright spot is zero in a negative pattern. In an example of the typical positive pattern when the ES probe is used, the number of the first bright spots is one, the number of the second bright spots is two, and the number of the fused bright spots is one. When the DF probe is used, in the state where the first image and the second image are superimposed, the number of the first bright spots is two, the number of the second bright spots is two, and the number of the fused bright spots is zero in the negative pattern. In an example of the typical positive pattern when the DF probe is used, the number of the first bright spots is one, the number of the second bright spots is one, and the number of the fused bright spots is two.

FIG. 9 shows examples of a reference pattern of a non-typical positive pattern of BCR/ABL fusion gene. One example of a non-typical positive pattern is a minor BCR/ABL pattern, and since a cleavage point of the BCR gene is located relatively upstream in the BCR gene, three first bright spots are detected for the ES probe. In another example of a non-typical positive pattern, a part of a binding region of a probe targeting the ABL gene of chromosome 9 is deleted, and depending on this, only one fused bright spot is detected although two fused bright spots are supposed to be detected when the DF probe is used. In another example of a non-typical positive pattern, a part of a binding region of the probe targeting the ABL gene of chromosome 9 and a part of a binding region of the probe targeting the BCR gene of chromosome 22 are deleted. Depending on this, only one fused bright spot is detected although two fused bright spots are supposed to be detected when the DF probe is used.

In addition to the BCR/ABL fusion gene, examples of chromosomal translocations for which a fused bright spot can be detected by the FISH method include AML1/ETO (MTG8) fusion gene (t(8;21)), PML/RARα fusion gene (t(15;17)), AML1 (21q22) translocation, MLL (11q23) translocation, TEL (12p13) translocation, TEL/AML1 fusion gene (t(12;21)), IgH (14q32) translocation, CCND1 (BCL1)/IgH fusion gene (t(11;14)), BCL2 (18q21) translocation, IgH/MAF fusion gene (t(14;16)), IgH/BCL2 fusion gene (t(14;18)), c-myc/IgH fusion gene (t(8;14)), FGFR3/IgH fusion gene (t(4;14)), BCL6 (3q27) translocation, c-myc (8q24) translocation, MALT1 (18q21) translocation, API2/MALT1 fusion gene (t(11;18) translocation), TCF3/PBX1 fusion gene (t(1;19) translocation), EWSR1 (22q12) translocation, and PDGFRβ (5q32) translocation.

Figure 10:
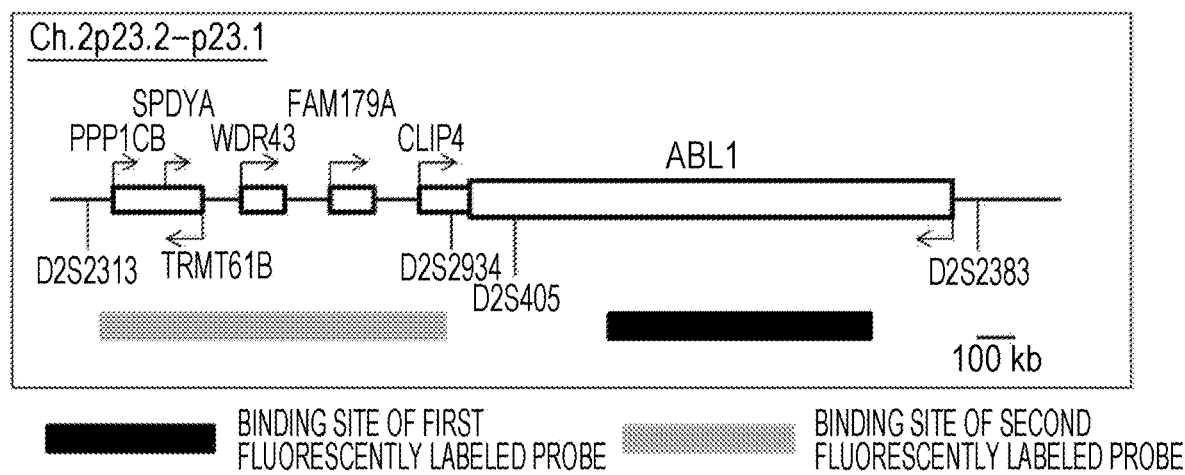
FIG. 10 is a diagram showing an example of a probe of an ALK locus.

FIG. 10 shows an example of a probe of the ALK locus. FIG. 11 shows examples of reference patterns of a negative pattern and a positive pattern in the case of detecting a chromosomal abnormality associated with the ALK locus. As shown in FIG. 10, the chromosomal abnormality of the ALK gene has a cleavage point near D2S405, and a part of the ALK gene is translocated to another site. For this reason, a first fluorescently labeled probe and a second fluorescently labeled probe are designed with the cleavage point therebetween. In a negative pattern shown in FIG. 11, since the ALK gene is not cleaved, two fused bright spots are present. In contrast, in a positive pattern, since the ALK gene is cleaved, only one fused bright spot is recognized (in the case where only one of the alleles is cleaved) or no fused bright spot is recognized (in the case where both of the alleles are cleaved). The negative pattern and the positive pattern are the same for the ROS1 gene and the RET gene in addition to the ALK gene.

Further, FIG. 11 shows examples of reference patterns of a chromosomal abnormality in which the long arm of chromosome 5 (5q) is deleted. For example, the first fluorescently labeled probe is designed to bind to the long arm of chromosome 5, and the second fluorescently labeled probe is designed to bind to the centromere of chromosome 5. In the negative pattern, since the number of centromere of chromosome 5 is the same as the number of long arm of chromosome 5, the number of the first bright spots and the number of the second bright spots are each two, reflecting the number of homologous chromosomes. In the positive pattern, long arm deletion occurs in one or both of chromosome 5 and the number of the first bright spots is only one or zero. This negative pattern and positive pattern are the same for deletion of short arm or long arm of other chromosomes. Examples of long arm deletion of other chromosomes include long arm deletion of chromosome 7 and chromosome 20. Other examples showing similar positive patterns and negative patterns include 7q31 (deletion), p16 (9p21 deletion analysis), IRF-1 (5q31) deletion, D20S108 (20q12) deletion, D13S319 (13q14) deletion, 4q12 deletion, ATM (11q22.3) deletion, and p53 (17p13.1) deletion.

Furthermore, FIG. 11 shows an example of trisomy of chromosome 8. The first fluorescently labeled probe binds to, for example, the centromere of chromosome 8. In the positive pattern, there are three first bright spots. In the negative pattern, there are two first bright spots. Such a bright spot pattern is the same for trisomy of chromosome 12. In chromosome 7 monosomy, for example, in the case of using the first fluorescently labeled probe that binds to the centromere of chromosome 7, the positive pattern has one first bright spot. In the negative pattern, there are two first bright spots.

Next, with reference to FIG. 5, details of step S3 in FIG. 3 will be described. First, in step S30, the processing unit 11 performs a process of selecting, from the plurality of reference patterns corresponding to the plurality of measurement items stored in the storage unit 12, a reference pattern corresponding to a measurement item of the sample 10. Then, in step S31, the processing unit 11 performs a process of comparing the bright spot pattern acquired for each cell with the negative pattern in the reference pattern selected according to the measurement item of the sample 10. The selection of the measurement item can be received by displaying a reception screen 30 for selecting a measurement item on the display unit 13, for example, as shown in FIG. 12. On the reception screen 30 of FIG. 12, a selection field 31 for selecting a measurement item for each of a plurality of cells to be analyzed (in the illustrated example, vertical 8 cells (A to H)×horizontal 12 cells (1 to 12)=96 cells) is provided, and a measurement item (for example, BCR/ABL fusion gene, ALK gene, or long arm deletion of chromosome 5) can be selected for each cell by a pull-down method. In FIG. 12, in addition to the measurement item, it is possible to select a probe by which the measurement item is further classified (for example, if the measurement item is BCR/ABL fusion gene, DF probe or ES probe) in the selection field 31.

The processing unit 11 reads out a reference pattern (a negative pattern and a positive pattern) corresponding to the measurement item or the probe in the measurement item selected on the reception screen 30 from the plurality of reference patterns corresponding to the plurality of measurement items stored in the storage unit 12 and compares the reference pattern with the bright spot pattern of the cell to be analyzed. When the bright spot pattern of the cell to be analyzed matches the negative pattern, the result of step S31 becomes YES, the process proceeds to step S32, and the cell is determined to be a normal cell. In contrast, when the bright spot pattern of the cell to be analyzed does not match the negative pattern, the result of step S31 becomes NO, the process proceeds to step S33, and the bright spot pattern is compared with the typical positive pattern. If the bright spot pattern matches the typical positive pattern, the result of step S33 becomes YES, the process proceeds to step S34, and the cell is determined to be a typical abnormal cell. In contrast, when the bright spot pattern does not match the typical positive pattern, result of step S33 becomes NO, the process proceeds to step S35, and the cell is determined to be a non-typical abnormal cell. The processing unit 11 repeatedly performs similar comparison processing on all of the cells to be analyzed, and makes determination of an abnormal cell or a normal cell for each cell. The processing unit 11 causes the storage unit 12 to store the result of determination of step S3 in FIG. 3 for each cell.

Returning to FIG. 3, next, in step S4, the processing unit 11 causes the display unit 13 to display information on the determination result of each cell to be analyzed. The processing unit 11 displays, for example, fluorescence images (composite images of the first images, the second images, and the third images) of cells determined to be abnormal cells, fluorescence images (composite images of the first images, the second images, and the third images) of cells determined to be normal cells on the display unit 13 as information associated with the determination result.

Figure 13:
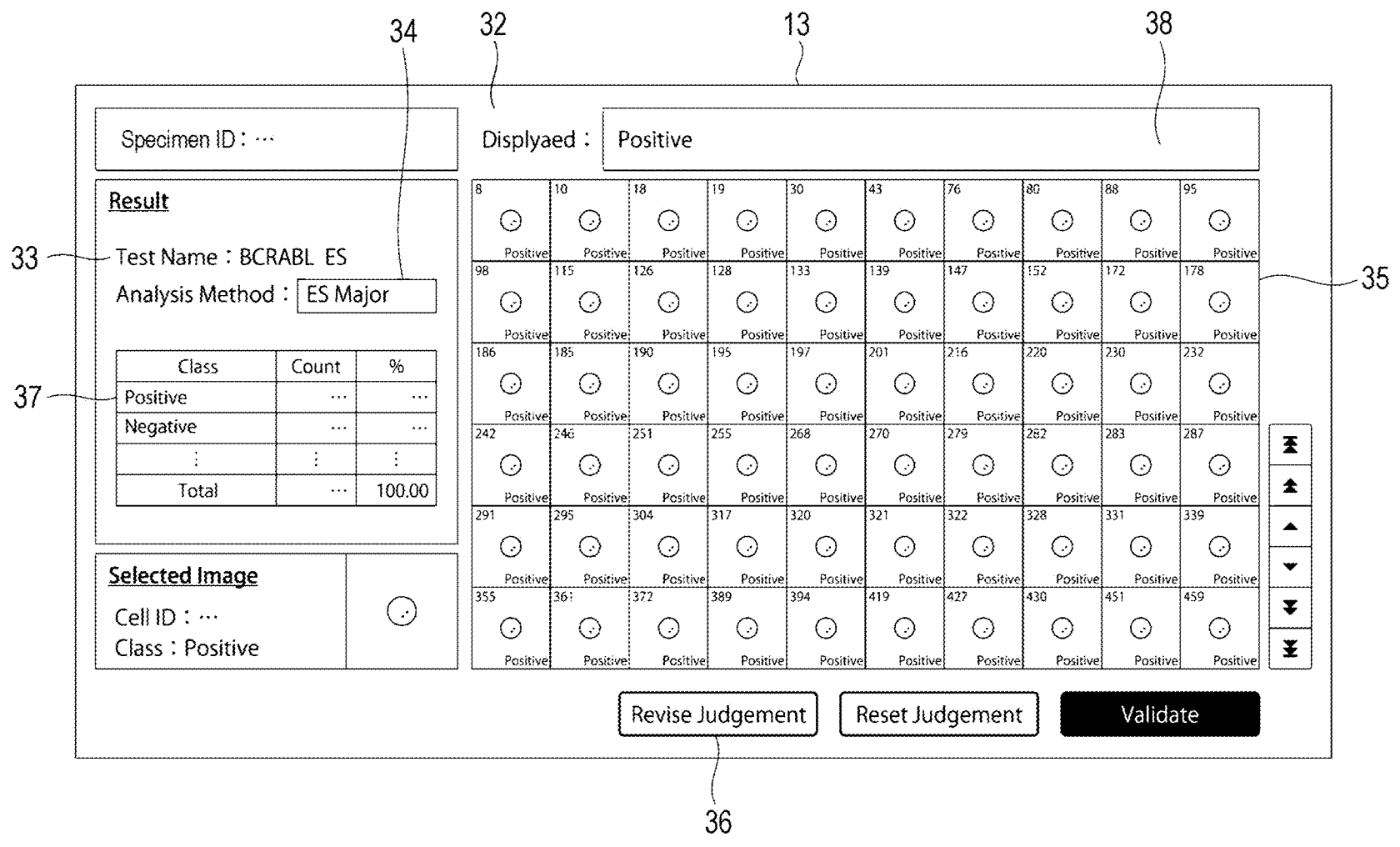

FIG. 13 is an example of an information display screen 32 of the display unit 13. On the information display screen 32 of FIG. 13, among the cells to be analyzed, fluorescence images are displayed in rows and columns for each cell detected based on a predetermined analysis method. On the information display screen 32, a measurement item 33 used for analyzing the cells is displayed, and an analysis method selection field 34 with which an analysis method can be selected is provided. In the analysis method selection field 34, it is possible to select whether to detect a typical abnormal cell (ES major pattern) or a non-typical abnormal cell (ES minor pattern, ES deception pattern) as an abnormal cell analysis method. On the information display screen 32, a displayed image selection field 38 is provided in which an option of displaying fluorescence images of cells determined to be abnormal cells (positive), an option of displaying fluorescence images of cells determined to be normal cells (negative), or an option of displaying fluorescence images of all the cells that have been analyzed can be selected by a pull-down method for the cells detected based on the analysis method selected in the analysis method selection field 34.

The processing unit 11 displays fluorescence images of cells selected in the displayed image selection field 38 in an image display field 35 of the display screen 32 for the cells detected based on the analysis method selected in the selection field 34. In the fluorescence image of cells displayed in the image display field 35, for each fluorescence image of a cell, a determination result of whether the cell is an abnormal cell (positive) or a normal cell (negative) is displayed in addition to a Cell ID. In FIG. 13, since an analysis method for detecting a typical abnormal cell (ES major pattern) is selected, when an option of displaying fluorescence images of cells determined to be abnormal cells (positive) in the displayed image selection field 38 is selected, fluorescence images of cells determined to be typical abnormal cells (ES major pattern) are displayed in the image display field 35. Fluorescence images of cells determined to be normal cells or fluorescence images of all the analyzed cells can be displayed according to the selection in the displayed image selection field 38.

As a result, an operator or the like can observe fluorescence images of cells determined to be abnormal cells on the display unit 13. When it is determined, by the observation by the operator or the like, that a cell that has been determined to be an abnormal cell is a normal cell, the processing unit 11 corrects, to a normal cell, the determination result of an abnormal cell selected as a normal cell by the operator or the like through the input unit 14 from among the fluorescence images of abnormal cells displayed on the display unit 13 and revised by a revision button 36. Then, the processing unit 11 stores the revised determination result in the storage unit 12. Similarly, when it is determined, by the observation by an observer such as the operator, that a cell that has been determined to be a normal cell is an abnormal cell, the processing unit 11 corrects, to an abnormal cell, the determination result of a normal cell selected as an abnormal cell by the operator or the like through the input unit 14 from among the fluorescence images of normal cells displayed on the display unit 13 and revised by the revision button 36. Then, the processing unit 11 stores the revised determination result in the storage unit 12. This improves the detection accuracy of abnormal cells and normal cells. The processing unit 11 can cause the display unit 13 to redisplay fluorescence images of cells determined to be abnormal or normal cells after revision.

Returning to FIG. 3, next, in step S5, the processing unit 11 generates information used for determination of the sample 10 based on a determination result on whether or not each cell is an abnormal cell.

For example, the processing unit 11 performs processing of generating, based on a result of analysis by the analysis method selected in the analysis method selection field 34, information of at least one of a group consisting of the number of abnormal cells, the ratio of the number of abnormal cells, the number of normal cells, and the ratio of the number of abnormal cells. The ratio of the number of abnormal cells and the ratio of the number of normal cells may be ratios to the number of all detected cells (the sum of the number of cells determined to be abnormal cells and the number of cells determined to be normal cells), or may be ratios to the total number of analyzed cells.

Then, in step S6 of FIG. 3, the processing unit 11 stores the information generated in step S5 in the storage unit 12 and displays the information on the display unit 13. For example, on the information display screen 32 of FIG. 13, a determination result field 37 is provided, and in the determination result field 37, the number and ratio of cells determined to be abnormal cells and the number and ratio of cells determined to be normal cells are displayed. In this case, since the analysis method for detecting a typical abnormal cell (ES major pattern) is selected in the analysis method selection field 34, the number and ratio of typical abnormal cells (positive) whose determination result is "G1R2F1" and the number and ratio of normal cells (negative) whose determination result is "G2R2F0" are displayed in the determination result field 37. In addition, when an analysis method for detecting a non-typical abnormal cell (ES minor pattern, ES deletion pattern) is selected in the analysis method selection field 34, the number and ratio of cells determined to be non-typical abnormal cells (positive) and the number and ratio of cells determined to be normal cells (negative) are displayed in the determination result field 37.

As a result, by referring to the information displayed in the information display screen 32, a doctor or the like can understand whether or not the sample 10 includes an abnormal cell and further the ratio of abnormal cells included in nucleated cells in the sample 10, and thus can determine with high accuracy whether the sample 10 is positive or negative.

As information to be used for determination of the sample 10, the processing unit 11 generates and displays on the display unit 13 various information such as character information such as "possibly positive?" or "possibly negative?" and other various information. "possibly positive?" is displayed when the ratio of abnormal cells is larger than a predetermined threshold value and the ratio of normal cells is smaller than a predetermined threshold value. When the ratio of normal cells is larger than a predetermined threshold value and the ratio of abnormal cells is smaller than a predetermined threshold value, "possibly negative?" is displayed.

As described above, according to the present disclosure, information to be used for determination of the sample 10 is generated based on the bright spot pattern of fluorescence of a fluorescence image acquired for each cell to be analyzed and a reference pattern corresponding to the measurement item of the sample 10 among reference patterns for respective measurement items. Therefore, it is unnecessary for the operator or the like to memorize many kinds of bright spot patterns indicating abnormal cells having chromosomal abnormalities to determine whether each cell is an abnormal cell, and the determination of abnormal cell does not depend on the sensation of the operator. Therefore, the determination accuracy of abnormal cells can be improved, and as a result, the accuracy of the information used for determination of the sample 10 can be improved.

Although one embodiment of the present disclosure has been described above, the present disclosure is not limited to the above-described embodiment, and various modifications are possible without departing from the gist of the present disclosure.

Figure 14:
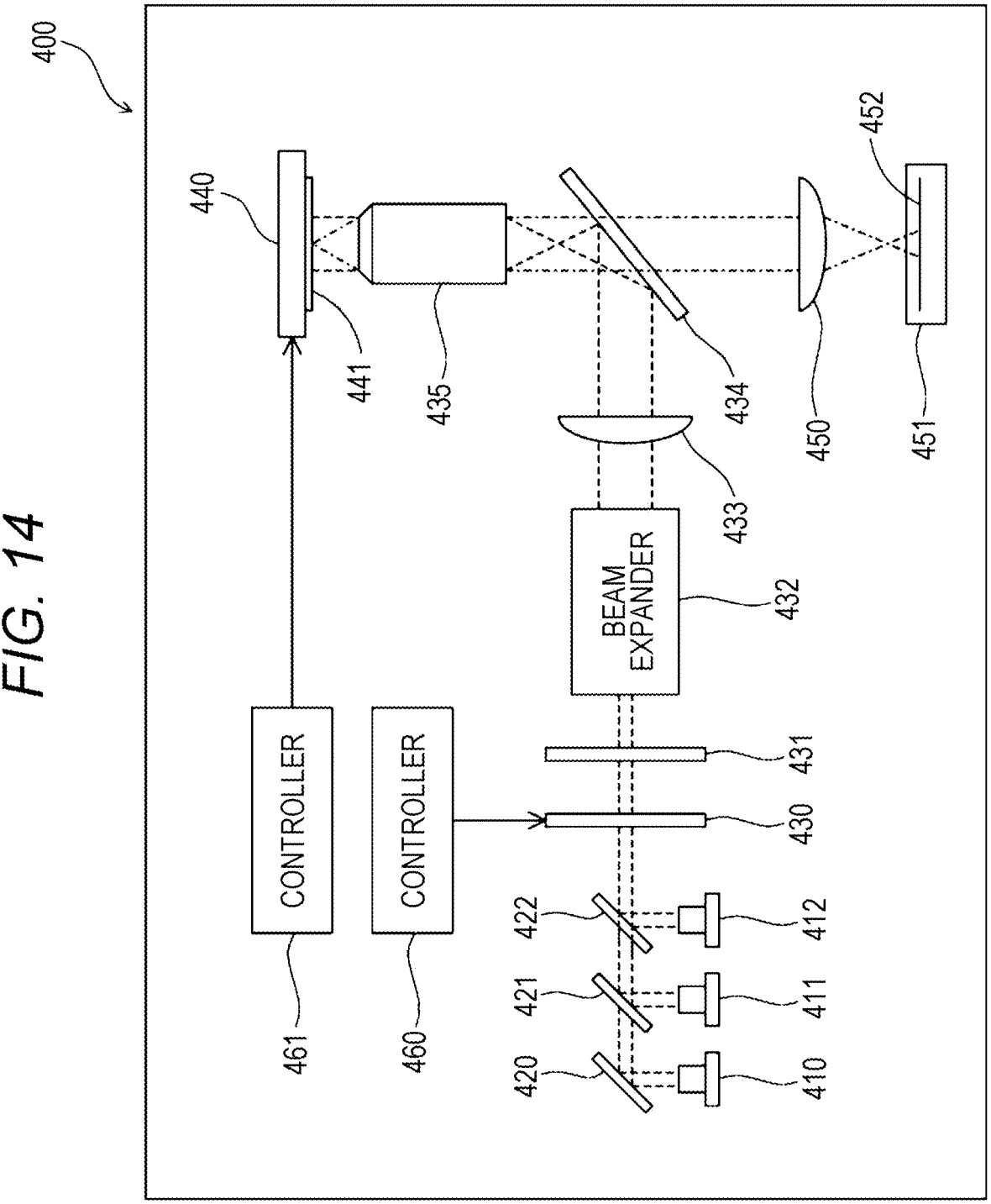
FIG. 14 is a schematic diagram showing a configuration of another example of a measurement device.

For example, in the above-described fluorescence image analyzing apparatus 1 of the present embodiment, the measurement device 100 shown in FIG. 1 may be replaced by a measurement device 400 including a fluorescence microscope shown in FIG. 14.

The measurement device 400 shown in FIG. 14 includes light sources 410 to 412, a mirror 420, dichroic mirrors 421 and 422, a shutter 430, a quarter-wave plate 431, a beam expander 432, a condenser lens 433, a dichroic mirror 434, an objective lens 435, a stage 440, a condenser lens 450, an imaging unit 451, and controllers 460 and 461. On the stage 440, a glass slide 441 is installed. On the glass slide 441, the sample 10 (shown in FIG. 1) prepared by the pretreatment in the pretreatment device 300 is placed.

The light sources 410 to 412 are respectively similar to the light sources 120 to 122 shown in FIG. 1. The mirror 420 reflects light from the light source 410. The dichroic mirror 421 transmits light from the light source 410 and reflects light from the light source 411. The dichroic mirror 422 transmits light from the light sources 410 and 411 and reflects light from the light source 412. The optical axes of the light from the light sources 410 to 412 are matched with each other by the mirror 420 and the dichroic mirrors 421 and 422.

The shutter 430 is driven by the controller 460 to switch between a state of transmitting light emitted from the light sources 410 to 412 and a state of blocking light emitted from the light sources 410 to 412. As a result of this, the irradiation time of the sample 10 with light is adjusted. The quarter-wave plate 431 converts linearly polarized light emitted from the light sources 410 to 412 into circularly polarized light. Fluorescent dye bound to a probe reacts to light of a predetermined polarization direction. Therefore, by converting excitation light emitted from the light sources 410 to 412 into circularly polarized light, the polarization direction of the excitation light becomes more likely to match the polarization direction to which the fluorescent dye reacts. This makes it possible to efficiently excite fluorescence in the fluorescent dye. The beam expander 432 expands a light irradiation area on the glass slide 441. The condenser lens 433 collects light so that the glass slide 441 is irradiated with parallel light from the objective lens 435.

The dichroic mirror 434 reflects light emitted from the light sources 410 to 412, and transmits fluorescence generated from the sample 10. The objective lens 435 guides the light reflected by the dichroic mirror 434 to the glass slide 441. The stage 440 is driven by the controller 461. The fluorescence generated from the sample 10 passes through the objective lens 435 and passes through the dichroic mirror 434. The condenser lens 450 collects the fluorescence transmitted through the dichroic mirror 434 and guides the light to an imaging surface 452 of the imaging unit 451. The imaging unit 451 captures an image of the fluorescence radiated on the imaging surface 452, and generates a fluorescence image. The imaging unit 451 is constituted by, for example, a charge coupled device (CCD).

The controllers 460 and 461 and the imaging unit 451 are connected to the processing unit 11 shown in FIG. 1, and the processing unit 11 controls the controllers 460 and 461 and the imaging unit 451 and receives the fluorescence image captured by the imaging unit 451. Unlike the case where the flow cell 110 is used as shown in FIG. 1, the fluorescence image captured by the imaging unit 451 may be in a state in which cells are in close contact with each other as shown in FIG. 2A. Therefore, the processing unit 11 performs a process of dividing the acquired fluorescence image for each nucleus of a cell, a process of setting a region corresponding to one nucleus of a cell in the fluorescence image, or the like.

Since three fluorescence images (first image to third image) can be acquired also in the measurement device 400 shown in FIG. 14 similarly to the present embodiment, whether the cell is an abnormal cell or a normal cell can be determined for each cell by extracting a bright spot pattern based on each fluorescence image for each cell and comparing the extracted bright spot pattern with a reference pattern for each cell.

Figure 15:
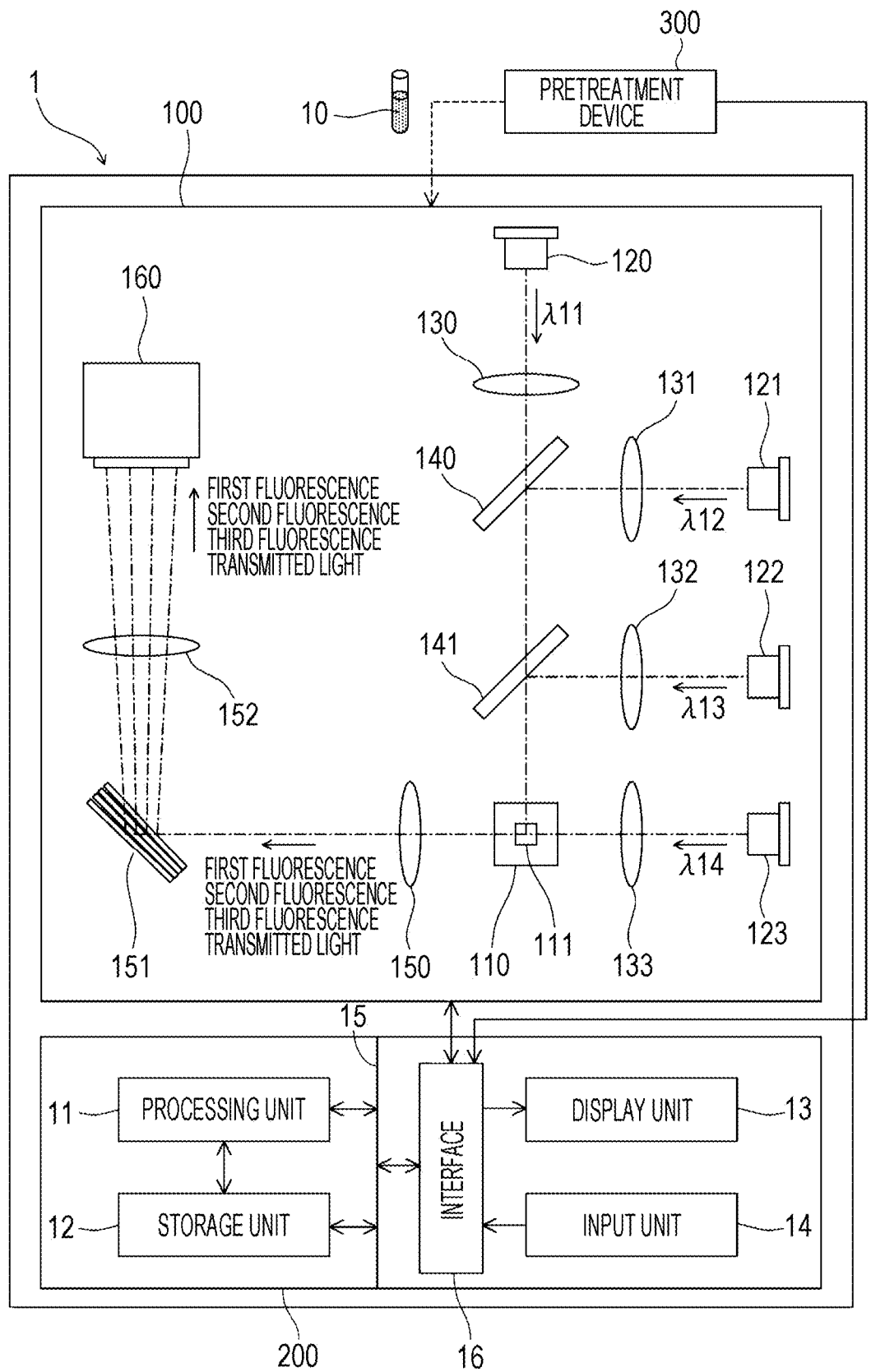
FIG. 15 is a schematic diagram showing a configuration of another embodiment of the fluorescence image analyzing apparatus.

As in the embodiment shown in FIG. 15, in the fluorescence image analyzing apparatus 1, the processing unit 11 may be connected to the pretreatment device 300 via the interface 16 so that data can be inputted and outputted therebetween. In this embodiment, the processing unit 11 can receive information associated with reagents including measurement items and probes as information from the pretreatment device 300. Accordingly, when the processing unit 11 selects the reference pattern corresponding to the measurement item of the sample 10 from the plurality of reference patterns corresponding to the plurality of measurement items stored in the storage unit 12 in step S30 of FIG. 5, the processing unit 11 may automatically read the reference pattern corresponding to the information associated with reagents including measurement items and probes transmitted from the pretreatment device 300 and the information on the reagent including the probe, and may compare the selected reference pattern with the bright spot pattern acquired for each cell in step S31.

Although the reference pattern is stored in advance in the storage unit 12 in the fluorescence image analyzing apparatus 1 in the above-described fluorescence image analyzing apparatus 1 of the present embodiment, the reference pattern may be acquired from an external server (not shown) via a network.

In the fluorescence image analyzing apparatus 1 of the present embodiment described above, the processing unit 11 may store the bright spot pattern of fluorescence in a newly acquired fluorescence image of an abnormal cell in the storage unit 12 as a reference pattern for each measurement item. The new reference pattern may be acquired by being input by a user via the input unit 14, or the processing unit 11 may acquire the new reference pattern from the external server (not shown) via the network.

A storage medium storing a computer program defining a processing procedure for processing the fluorescence images of cells by the processing unit 11 of the processing device 200 described above can also be provided.

What is claimed is:
1. An analyzing method comprising:
receiving, by a processing device, an identification of a measurement item of a sample including cells;
obtaining, by the processing device, a fluorescence image of each of the cells labeled with a fluorescent dye at a target site;
generating, by the processing device, a pixel representation of each of the fluorescence images, the pixel representation comprising pixel values of pixels constituting the fluorescence image;
acquiring, by the processing device, a bright spot pattern of each of the fluorescence images based on pixel values in the pixel representation of the fluorescene image;
comparing, by the processing device, the bright spot pattern with a reference pattern corresponding to the measurement item based on coordinate information of pixels included in a bright spot of the bright spot pattern, wherein the bright spot pattern comprises at least one of a positive reference pattern and a negative reference pattern;
classifying, by the processing device, the acquired bright spot pattern based on the comparison of the reference pattern and the acquired bright spot pattern; and
displaying information of the sample based on a classification of the acquired bright spot pattern for a plurality of cells of the sample.
2. The method according to claim 1, wherein the reference pattern includes a combination of a positive pattern and a negative pattern.

3. The method according to claim 2, wherein the combination includes a typical positive pattern and a non-typical positive pattern.

4. The method according to claim 2, further comprising:
counting, as positive cells, cells whose image has the positive pattern corresponding to the identified measurement item,
wherein the information of the sample includes at least one of a number of positive cells and a ratio of the number of positive cells among a population.

5. The method according to claim 4, further comprising:
counting, as negative cells, cells whose image has the negative pattern corresponding to the identified measurement item,
wherein the information of the sample includes at least one of a number of negative cells and a ratio of the number of negative cells among the population.

6. The method according to claim 1, wherein the bright spot pattern is a number of bright spots per color in the fluorescence image.

7. The method according to claim 1, wherein the reference pattern is a number of bright spots per color.

8. The method according to claim 1, wherein the measurement item is related to a translocation of a target gene, a deletion of the target gene, an inversion of the target gene, or a duplication of the target gene.

9. The method according to claim 8, wherein the measurement item is at least one selected from a group consisting of BCR/ABL fusion gene, AML1/ETO (MTG8) fusion gene, PML/BARa fusion gene, TEL/AML1 fusion gene, ALK gene, long arm deletion of chromosome 5, long arm deletion of chromosome 7, and long arm deletion of chromosome 20.

10. The method according to claim 9, wherein the measurement item is further classified by probes to hybridize to the target site.

11. The method according to claim 2, wherein the positive pattern has a fused bright spot including a first bright spot and a second bright spot overlapped in the fluorescence image.

12. A device for analyzing a fluorescence image comprising:
a light source that emits light to a sample including cells labeled with a fluorescent dye at a target site;
an imaging unit configured to capture a fluorescence image of each of the cells that emit fluorescence by being irradiated with the light;
a display; and
a processor, wherein the processor is configured to:
generate a pixel representation of the captured fluorescence image, the pixel representation comprising pixel values of pixels constituting the captured fluorescence image;
process the captured fluorescence image to acquire a bright spot pattern of the fluorescence image based on pixel values in a pixel representation of the captured fluorescence image;
compare the bright spot pattern with a reference pattern corresponding to the measurement item based on coordinate information of pixels included in a bright spot of the bright spot pattern, wherein the bright spot pattern comprises at least one of a positive reference pattern and a negative reference pattern;
classify the acquired bright spot pattern based on the comparison of the reference pattern and the acquired bright spot pattern; and
control the display to display information of the sample based on a classification of the acquired bright spot pattern for a plurality of cells of the sample.

13. The device according to claim 12 wherein the reference pattern includes a combination of a positive pattern and a negative pattern.

14. The device according to claim 13, wherein the combination includes a typical positive pattern and a non-typical positive pattern.

15. The device according to claim 13, wherein
the processor is configured to count, as positive cells, cells whose image has the positive pattern corresponding to the measurement item,
the information of the sample includes at least one of a number of positive cells and a ratio of the number of positive cells among a population.

16. The device according to claim 15, wherein
the processor is configured to count, as negative cells, cells whose image has the negative pattern corresponding to the identified measurement item,
the information of the sample includes at least one of a number of negative cells and a ratio of the number of negative cells among the population.

17. The device according to claim 12, wherein the bright spot pattern is a number of bright spots per color in the fluorescence image.

18. The device according to claim 12, wherein the reference pattern is a number of bright spots per color.

19. The device according to claim 15, wherein the processor is configured to:
process the captured fluorescence image to acquire the bright spot pattern of the fluorescence image in part by comparing pixel values in the fluorescence image to a threshold value to determine a boundary between a bright spot of the bright spot pattern and a background in the fluorescence image.

20. The method according to claim 1, wherein acquiring the bright spot pattern of each of the fluorescence images further comprises:
extracting a plurality of bright spots from the fluorescence image;
comparing a position of a nucleus region with a position of the plurality of bright spots; and
excluding a bright spot with a position outside of the nucleus region from the bright spot pattern.

* * * * *

UNITED STATES PATENT AND TRADEMARK OFFICE
CERTIFICATE OF CORRECTION

PATENT NO. : 11,946,866 B2
APPLICATION NO. : 17/345645
DATED : April 2, 2024
INVENTOR(S) : Kazuhiro Yamada et al.

It is certified that error appears in the above-identified patent and that said Letters Patent is hereby corrected as shown below:

In the Claims

Column 18, Claim 1, Line 50, delete "fluorescene" and replace with --fluorescence--.

Column 19, Claim 9, Line 29, delete "PML/BARa" and replace with --PML/BARα--.

Signed and Sealed this
Fourth Day of June, 2024

Katherine Kelly Vidal
*Director of the United States Patent and Trademark Office*